(12) United States Patent
Pascual-Leone et al.

(10) Patent No.: US 9,849,300 B2
(45) Date of Patent: Dec. 26, 2017

(54) TRANSCRANIAL MAGNETIC STIMULATION (TMS) METHODS AND APPARATUS

(71) Applicants: Beth Israel Deaconess Medical Center, Inc., Boston, MA (US); Children's Medical Center Corporation, Boston, MA (US)

(72) Inventors: Alvaro Pascual-Leone, Wayland, MA (US); Alexander Rotenberg, Brookline, MA (US); Iain Glass, West Vancouver (CA); Frances E. Jensen, Chestnut Hill, MA (US)

(73) Assignees: Children's Medical Center Corporation, Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 13/744,869

(22) Filed: Jan. 18, 2013

(65) Prior Publication Data
US 2013/0338424 A1    Dec. 19, 2013

Related U.S. Application Data

(63) Continuation of application No. 12/312,931, filed as application No. PCT/US2007/024694 on Dec. 1, 2007, now abandoned.
(Continued)

(51) Int. Cl.
*A61N 2/00* (2006.01)
*A61N 2/02* (2006.01)
(Continued)

(52) U.S. Cl.
CPC ............ *A61N 2/006* (2013.01); *A61B 5/4094* (2013.01); *A61N 2/02* (2013.01); *A61B 5/0006* (2013.01);
(Continued)

(58) Field of Classification Search
CPC . A61B 5/0006; A61B 5/04001; A61B 5/0476; A61B 19/203; A61B 5/0482; A61N 2/02; A61N 2/006; A61N 2/008
(Continued)

(56) References Cited

U.S. PATENT DOCUMENTS 6,198,958 B1    3/2001    Ives et al.
6,266,566 B1    7/2001    Nichols et al.
(Continued)

FOREIGN PATENT DOCUMENTS

WO    WO 2007103475 A2    9/2007

OTHER PUBLICATIONS

International Search Report for Written Opinion for Application No. PCT/US2007/024694 dated Aug. 13, 2008.
(Continued)

*Primary Examiner* — Navin Natnithithadha
*Assistant Examiner* — Sunita Reddy
(74) *Attorney, Agent, or Firm* — Wolf, Greenfield & Sacks, P.C.

(57) ABSTRACT

Method and devices are provided for treating subjects with Transcranial Magnetic Stimulation (TMS). According to some approaches, the methods and devices are configured for the treatment of ongoing seizures. Other approaches relate to the use of TMS as an antiepileptogenic or for use in determining preferential placement of intracranial probes.

21 Claims, 15 Drawing Sheets

Related U.S. Application Data

(60) Provisional application No. 60/872,207, filed on Dec. 1, 2006.

(51) Int. Cl.
| | |
|---|---|
| A61B 5/00 | (2006.01) |
| A61B 5/04 | (2006.01) |
| A61B 5/0476 | (2006.01) |
| A61B 5/0482 | (2006.01) |
| A61B 90/14 | (2016.01) |

(52) U.S. Cl.
CPC ......... *A61B 5/04001* (2013.01); *A61B 5/0476* (2013.01); *A61B 5/0482* (2013.01); *A61B 90/14* (2016.02); *A61N 2/008* (2013.01)

(58) Field of Classification Search
USPC ............... 600/14, 15, 13, 544; 128/897–899
See application file for complete search history.

(56) References Cited

U.S. PATENT DOCUMENTS

| | | | |
|---|---|---|---|
| 6,473,639 | B1 * | 10/2002 | Fischell et al. ............... 600/544 |
| 6,571,123 | B2 | 5/2003 | Ives et al. |
| 2002/0103512 | A1 * | 8/2002 | Echauz et al. ................... 607/9 |
| 2002/0169373 | A1 | 11/2002 | Kuth |
| 2003/0028072 | A1 * | 2/2003 | Fischell et al. ................. 600/13 |
| 2003/0050527 | A1 | 3/2003 | Fox et al. |
| 2004/0138578 | A1 * | 7/2004 | Pineda et al. ................. 600/544 |
| 2005/0148808 | A1 | 7/2005 | Cameron et al. |
| 2005/0234286 | A1 | 10/2005 | Riehl et al. |
| 2006/0122496 | A1 | 6/2006 | George et al. |
| 2010/0210894 | A1 | 8/2010 | Pascual-Leone et al. |
| 2011/0224571 | A1 | 9/2011 | Pascual-Leone et al. |
| 2015/0119689 | A1 | 4/2015 | Pascual-Leone et al. |

OTHER PUBLICATIONS

International Preliminary Report on Patentability for Application No. PCT/US2007/024694 dated Jun. 3, 2009.

* cited by examiner

Obscured EEG for 6 seconds with conventional recording methods.

TMS artifact limited to <100 msec. with preamplifier signal processing.

Treated and untreated spontaneous seizures. Ongoing
EEG permits real-time assesment of TMS anticonvulsant
effect.

Sample aborted kainate-induced seizure.
TMS was applied as soon as an ictal EEG pattern
was recognized.

Rat treated with KA only (n=2)

KA and 0.5Hz rTMS (n=2)

Untreated control (n=2)

Kainate-induced seizure terminated during 0.75 Hz rTMS. 60-sec. EEG tracing shows ongoing seizure ending after 15 stimuli.

Mimal rTMS artifact on EEG. 15-sec. tracing shows terminating seizure in a patient with focal epilepsy. Real-time analysis of the ictal state is permitted as 1 Hz rTMS artifact (vertical lines) does not obscure EEG.

TRANSCRANIAL MAGNETIC STIMULATION (TMS) METHODS AND APPARATUS

This application is a continuation of U.S. application Ser. No. 12/312,931 filed Apr. 30, 2010 which is a U.S. National Stage Application No. PCT/US2007/024694 filed Dec. 7, 2007, which claims the benefit of U.S. provisional Application Ser. No. 60/877,207 filed Dec. 1, 2006, which applications are hereby incorporated by reference to the maximum extent allowable by law.

FIELD

The present invention relates to transcranial magnetic stimulation (TMS).

DISCUSSION OF RELATED ART

Transcranial magnetic stimulation (TMS) provides a non-invasive procedure for generating fluctuating magnetic fields to induce stimulating intracranial electric current to desired areas of the human body, typically targeted areas of the brain. In general, TMS procedures involve identifying a discrete region of the brain and focusing fluctuating magnetic fields generated by one or more coils positioned proximate the head at a location that induces electric current in the identified region of the brain. The type and character of the fluctuating magnetic field deposition, and the location of the targeted region of the brain typically depends on the type of therapeutic and/or diagnostic application that is to be achieved.

A growing understanding of TMS techniques has led to the development of numerous diagnostic and therapeutic applications in neurology, cognitive neuroscience, clinical neurophysiology, psychiatry, neurorehabilitation, etc. Repetitive Transcranial Magnetic Stimulation (rTMS) has been used as noninvasive treatment for a variety of medical conditions. Applications for rTMS include, but are not limited to, psychiatric disorders, such as depression, hallucinations, obsessions, and drug craving; neurologic diseases such as Parkinson's disease, or dystonia; rehabilitation of aphasia or of hand function after stroke; and pain syndromes, such as caused by migraine, neuropathies, low back pain, or internal visceral diseases such as chronic pancreatitis or cancer. As used herein, the term TMS refers generically to both TMS and rTMS.

For many conventional applications, effective rTMS has included routine stimulation according to a prescribed schedule. For example, a particular therapeutic application may have the best results when repeated for several days (e.g., ten to twenty days) on a daily or even bi-daily regimen. Other applications may require more or less frequent stimulation and/or require different lengths of time over which the stimulation is repeated. For example, the prescribed length of time may vary from a couple of days, to several weeks, months or years. In some circumstances, the most effective treatment may involve an indefinite stimulation regimen. In particular, after the initial treatment (referred to as the induction phase), a subject may require (or respond more positively) by continuing with maintenance therapy for many months, and possibly indefinitely.

SUMMARY

According to one aspect of the invention, a system for applying transcranial magnetic stimulation to a subject is disclosed. The system comprises an electromagnetic coil configured to deliver a fluctuating magnetic field to a subject's brain to induce an electric current therein. An interface is configured to position the electromagnetic coil in proximity to the brain of the subject. A controller controls operation of the electromagnetic coil according to an operating protocol. The operating protocol comprises delivering an initial fluctuating magnetic field having an intensity and a duration and delivering a subsequent fluctuating magnetic field after delivering the initial fluctuating magnetic field. At least one of intensity and duration of the subsequent fluctuating magnetic field is greater than the intensity and duration of the initial fluctuating magnetic field, respectively.

Another aspect of the invention relates to a portable device for applying transcranial magnetic stimulation to a subject. The device comprises a portable power source, an electromagnetic coil that receives power from the power source to produce a fluctuating magnetic field that may induce an electric current in a subject's brain. A controller controls operation of the electromagnetic coil according to an operating protocol. A housing houses the electromagnetic coil and positions the electromagnetic coil to deliver the fluctuating magnetic field to a subject's brain.

Another aspect of the invention relates to a device for treating an ongoing seizure. The device comprises an electromagnetic coil that receives power from a power source to produce a fluctuating magnetic field. A controller controls operation of the electromagnetic coil according to an operating protocol. A plurality of electrodes receive a signal indicative of brain activity in the subject and provide the electrical signal to the controller. The device also comprises an interface that includes the plurality of electrodes and the electromagnetic coil. The interface is configured to position the plurality of electrodes to receive the signal and to position the electromagnetic coil to deliver the fluctuating magnetic field to a subject's brain.

Another aspect of the invention relates to a method of non-invasively assessing intracranial electrode positioning or similarly, guiding placement of intracranial electrodes. The method comprises positioning an electromagnetic coil at an initial external position about a subject's brain. A fluctuating magnetic field is applied from the electromagnetic coil positioned at the initial external position about the subject's brain. Any effects exhibited by the subject subsequent to applying the first fluctuating magnetic field from the electromagnetic coil at the initial external position are identified. The electromagnetic coil is repositioned at a subsequent external position, different than the initial external position, about the subject's brain. A subsequent fluctuating magnetic field is applied from the electromagnetic coil positioned at the subsequent external position about the subject's brain. Any effects exhibited by the subject subsequent to applying the subsequent fluctuating magnetic field from the electromagnetic coil at the subsequent external position are identified. Any effects associated with applying the fluctuating magnetic field from the first external position of the electromagnetic coil and any effects associated with applying the fluctuating magnetic field from the subsequent external position and then compared to identify a preferential position among the initial and subsequent external positions. The effects that are assessed may be intended, desirable therapeutic effects or may be unintended and undesirable side effects. This procedure may be repeated multiple times, effectively probing for desirable and undesirable effects associated with multiple scalp (and thus brain) regions. A detailed map may be generated of the likelihood of brain stimulation to induce desirable and undesirable effects in the subject when targeting different regions of the brain.

Another aspect of the invention relates to a method of terminating an ongoing seizure. The method comprises identifying a subject for treatment and positioning an electromagnetic coil about the seizing subject's brain. The electromagnetic coil is energized to direct a fluctuating magnetic field from the electromagnetic coil to the seizing subject's brain.

Another aspect of the invention relates to a method of preventing epilepsy. The method comprises identifying an epilepsy precipitating occurrence or predisposition (genetic or acquired) and exposing a brain of the subject to rTMS.

Further features and advantages of the present invention, as well as the structure of various embodiments of the present invention are described in detail below with reference to the accompanying drawings.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which.

DETAILED DESCRIPTION

Figure 1:
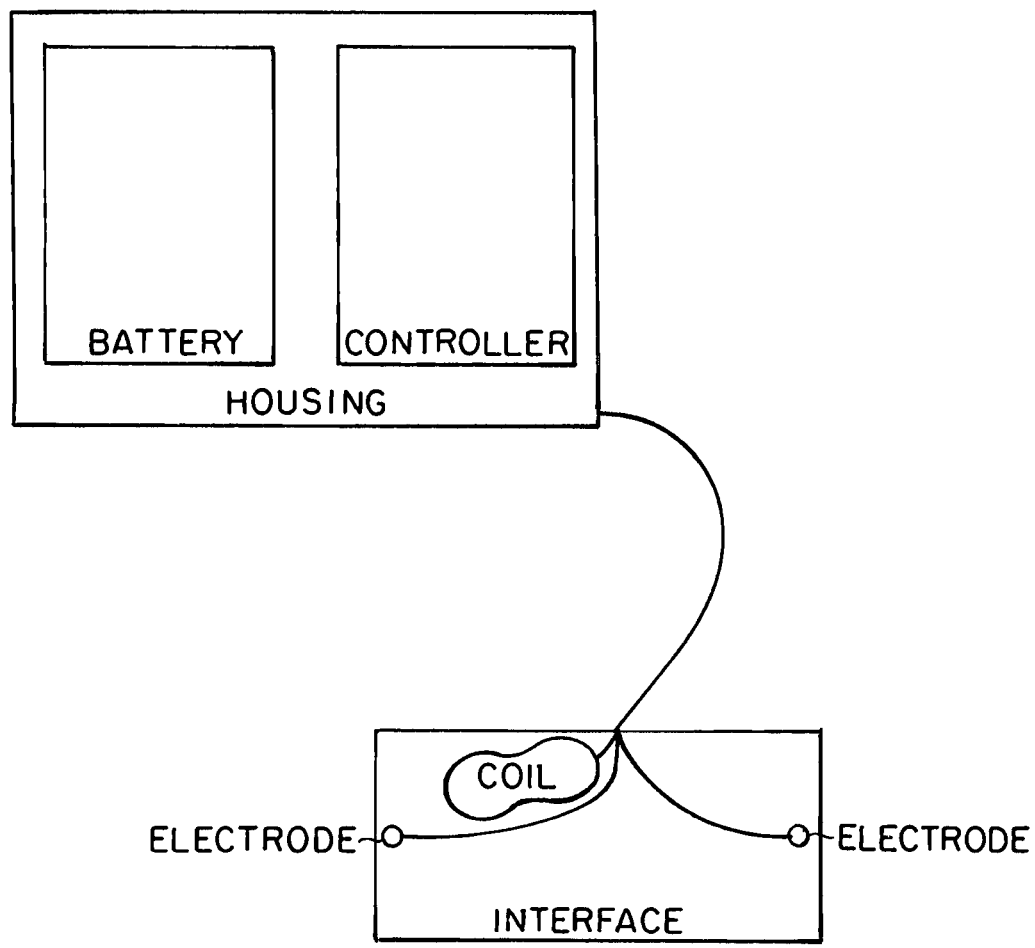
FIG. 1 illustrates, schematically, components that are common to several embodiments of the present invention.

As discussed herein, the applicants have appreciated that TMS may provide benefits in some emergent settings, such as in the treatment of an ongoing seizure.

Aspects of the invention relate to novel uses for TMS, and devices that facilitate the use of TMS in particular settings. Embodiments of the TMS device may comprise electromagnetic coil(s) that, when energized, emit a magnetic field either as a single pulse of magnetic energy or as magnetic energy that fluctuates in intensity or polarity. The magnetic field may be applied to the brain of a subject to induce an electric current therein, which, in turn, may stop an ongoing seizure (as used herein, the term "magnetic field" refers generally to the stimulation that may be applied to a subject's brain in TMS). The electromagnetic coil may be housed in an interface that facilitates quick and easy positioning of the coil proximate to a subject's brain. A controller may be provided that runs the electromagnetic coil according to a defined, operating protocol that further simplifies use of the device.

One aspect of the invention relates to the treatment of an ongoing seizure with TMS. Generally speaking, during a seizure, electric signals are transmitted about the brain in an abnormal, systematic manner, unlike the more chaotic signals that typify normal brain activity. The applicants have appreciated that inducing an electric current in a subject's brain during a seizure may disrupt systematic signal transmission and, in doing so, may cause termination of the ongoing seizure.

Another aspect of the invention relates to an apparatus for performing TMS according to an escalating, operating protocol. It may be difficult to define, a priori, the intensity, duration and/or frequency of magnetic field(s) that may be required to stop a seizure in a given subject, without also over-exposing the subject. In this regard, the applicants have appreciated that applying a magnetic field in an escalating manner can minimize the subject's exposure to the magnetic field having the intensity, duration and/or frequency that is necessary to stop the seizure. It is to be appreciated, however, that an escalating protocol may be used in conjunction with TMS for purposes other than stopping an ongoing seizure, such as treating epilepsy or preventing the onset of epilepsy, or other therapeutic applications of TMS in neurology, psychiatry, or rehabilitation.

Another aspect of the invention relates to an apparatus configured to perform TMS in an emergent setting. As may be appreciated, subjects may begin seizing unexpectedly, even when under the care of a doctor or other healthcare professional. Embodiments of the TMS apparatus may be portable and/or readily deployable to facilitate use in such situations. Some embodiments may be configured for placement in highly trafficked, public venues, such as airports, malls, and the like, such as where defibrillator devices are now commonly found. Illustrative embodiments may include other features, such as a portable power source, that further facilitate ready deployment and use. It is to be appreciated, however, that the use of such devices is not limited to emergent settings, and that such devices may be used for other purposes, such as administering TMS as an antiepileptogenic, or applying TMS for treatment of a variety of other diseases in the field.

Yet another aspect of the invention relates to methods of non-invasively assessing positions of a subject's brain for the placement of stimulating intracranial electrodes, and identifying preferential or optimal position(s). Candidate positions for the invasive placement of intracranial electrodes may first be identified. The fluctuating magnetic field (i.e., the stimulation) from embodiments of the TMS device may be focused to the candidate positions to induce current at the candidate positions one at a time in a systematic manner. The subject may be observed for the presentation of any desirable and undesirable (intended and unintended) effects associated with focusing the induced current at each of the candidate positions. Candidate positions may then be compared, based on the existence or extent of effects (desirable or undesirable), such that preferred positions may be identified for further consideration. The effectiveness of stopping ongoing seizures by applying fluctuating magnetic fields to each of the preferred positions, as well as the potential risk of undesirable effects and adverse effects of the stimulation may then be evaluated prior to performing an invasive procedure to implant an intracranial electrode at one or more of the preferred positions. In this manner, a noninvasive method may serve to guide and optimize the placement of invasive electrode(s), thus increasing the efficacy and reducing the risk of adverse effects for the subject.

Yet another aspect of the invention relates to methods of using TMS as an antiepileptogenic to prevent the onset of epilepsy. A healthcare profession may prescribe rTMS after identifying an event, such as a head trauma, or diagnosing a condition that predisposes a subject to epilepsy, such as autism or tuberous sclerosis, or finding a genetic predisposition that might precipitate or will eventually result in the onset of epilepsy or epileptogenesis in a particular subject. TMS may then be administered according to a variety of protocols, as discussed herein, to prevent the onset of epilepsy.

Turn now to the figures, and initially FIG. 1, which shows components that are common to many embodiments of the TMS device. An electromagnetic coil, typically in the shape of a "figure-eight", is connected to a power supply that, when activated, energizes the coil. Operation of the electromagnetic coil may be governed by a controller that is programmable or that includes a single, operating protocol that defines how, when, and to what extend the coil is energized.

FIG. 1 also shows electrodes that may be placed about a subject's head to detect electric signals indicative of brain activity, in the same manner as an electroencephalogram (EEG), as is discussed in greater detail herein. The electrodes and the electromagnetic coil may be incorporated into an interface configured for placement about a subject's head to facilitate rapid placement of both the coil and electrodes, as may be required in an emergent setting.

The applicant has appreciated that a generally portable TMS device may facilitate more convenient application of and/or completion of TMS treatment. For example, a portable TMS device may facilitate the use of TMS treatment in an emergent situation, whereas systems constructed of independent components might involve additional set up that can delay the application of TMS treatment and the termination of an ongoing seizure. As discussed herein, seizures may cause brain damage and the risk of brain damage may increase with the duration of a seizure. A TMS device with features that reduce the time required for deployment and use may prevent or reduce the extent of brain damage that occurs in a seizing subject.

Seizures are often characterized by the abnormal, systematic transmission of electric signals in a subject's brain. Often, a seizure begins with the systematic transmissions of signals in a discrete portion of the subject's brain, such as a discrete portion of the cerebral cortex. As the seizure progresses, larger portions of the subject's brain experience the systematic transmission of electric signals. This process often leads to the entire brain being overcome with abnormal, systematic transmissions of electric signals. In this respect, focusing of a fluctuating magnetic field may not be required for the fluctuating magnetic field to be incident on an affected portion of a subject's brain. Electromagnetic coils may simply be positioned to subject a portion or all of a subject's brain to the fluctuating magnetic field.

Illustrative embodiments may include a portable power source to facilitate rapid deployment of the TMS device. As shown in FIG. 1, the portable power source may include a battery pack that is incorporated directly into the TMS device. The battery pack may provide a primary source of power to the electromagnetic coil, controller, and other components of the device. Such a configuration may prove useful for TMS devices that are made available in high traffic areas, like shopping malls, airports, and the like; or that are made available in places were customary medical assistance is not readily available, like in airplanes, ferries, etc. It is to be appreciated, however, that not all embodiments of TMS devices require a portable power source, and that some embodiments may include portable power sources for secondary or backup power or no portable power sources at all.

The portable power source may be rechargeable, replaceable or disposable, as aspects of the invention are not limited in this respect. A rechargeable power source may facilitate using the TMS device multiple times. According to some embodiments, a TMS device positioned for public access may, while stored, be plugged into a wall outlet to ensure that the portable power source remains fully charged. Such embodiments may be removed from the stored position and unplugged for use, if necessary.

Illustrative embodiments may comprise a common power source to energize the electromagnetic coil(s) and to provide power to controls, displays, and other components of a TMS device. However, it is to be appreciated that the invention is not limited in this respect, as embodiments may include separate power supplies, portable or otherwise, for energizing the coil and providing power to other components of a TMS device.

Figure 2A:
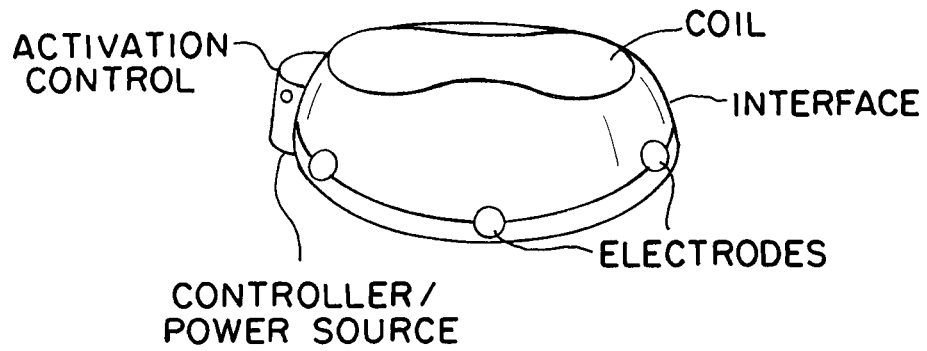
FIG. 2A-2C illustrate various embodiments of portable devices configured to administer TMS.

An interface may incorporate one or more electromagnetic coils such that, during use, the coil(s) are positioned to deliver a magnetic field to a substantial portion of a seizing subject's brain. According to the embodiment illustrated in FIG. 2A, the interface includes a pliable hat-shaped device that can be fitted rapidly to most any subject's head.

Figure 2B:
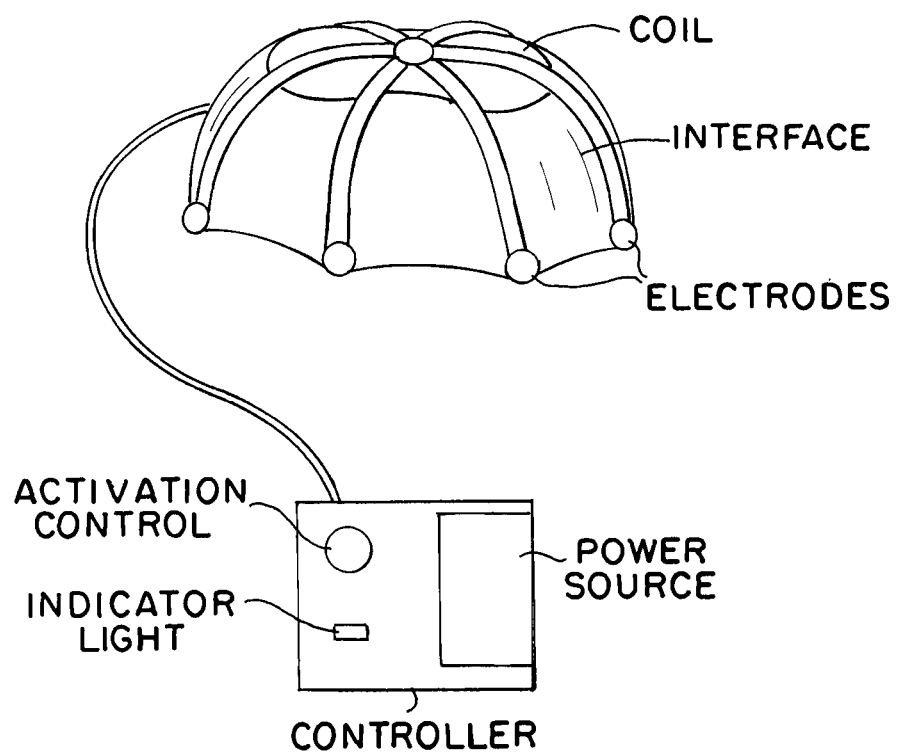

Alternately, as shown in the embodiment of FIG. 2B, the interface may comprise a pliable envelope with flexible, resilient bands that, when worn by a subject, extend downward from the subject's crown toward the subjects hairline. These bands may be expanded so that the interface can slide over a subject's head, positioning the electromagnetic coil(s) to deliver a magnetic field to the subjects brain.

Figure 2C:
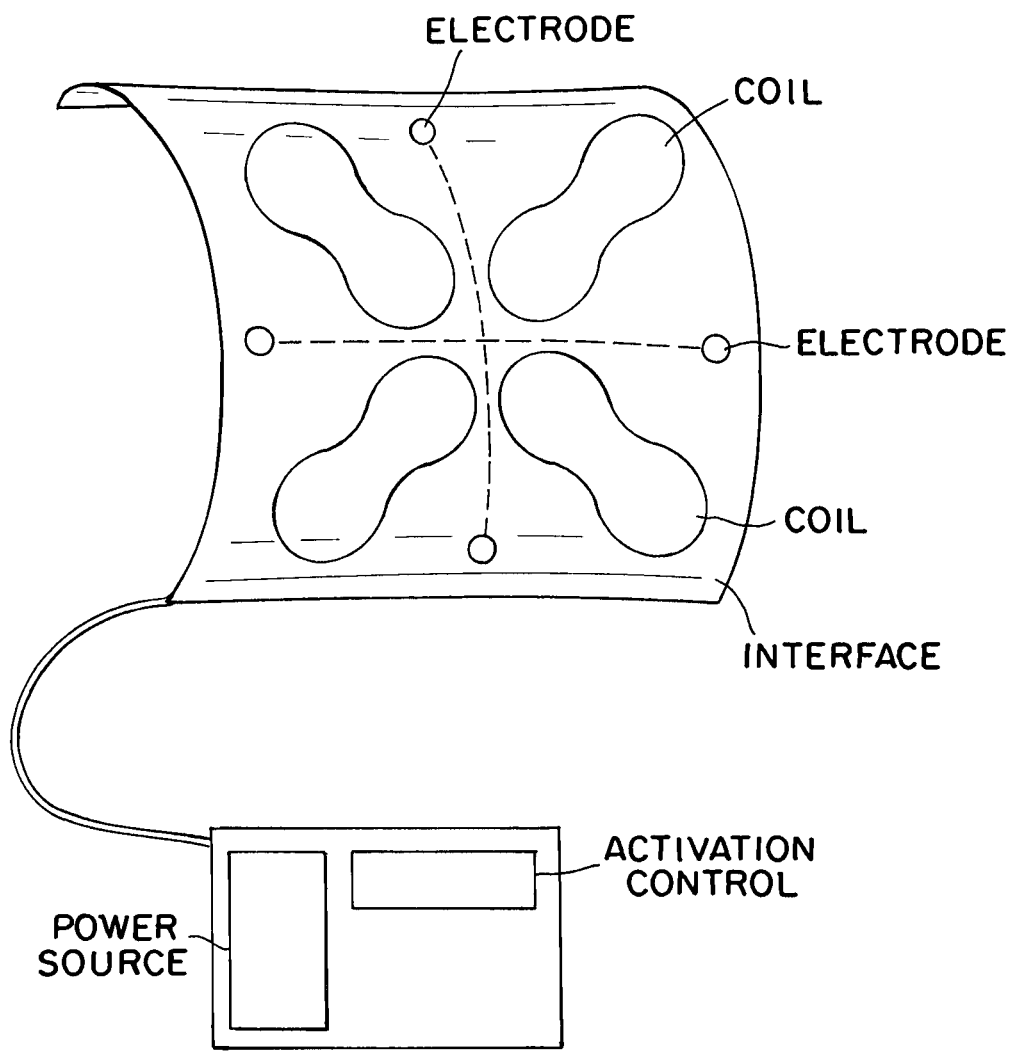

FIG. 2c shows yet another embodiment of an interface that may be used to rapidly position an electromagnetic coil about a subject's head. As shown, the interface comprises a pliable envelope, such as might be made of cloth, plastic, and the like. The interface may be held in place by a healthcare professional, or other respondent, as the TMS device is activated to deliver a fluctuating magnetic field to the subject's brain to induce electrical currents therein. It is to be appreciated, however, that other embodiments may also be constructed for rapid positioning of a coil about a subjects brain, as aspects of the invention are not limited to those embodiments shown in FIGS. 2A-2C.

Embodiments of the TMS device may include a single electromagnetic coil, or a plurality of electromagnetic coils for delivering a fluctuating magnetic field to subject's brain to induce electric current or impulses therein. By way of example, the embodiment of FIG. 2c shows four, electromagnetic, "figure-eight" shaped coils positioned within or on the envelope. The coils are positioned about the interface such that, during use, each of the coils is positioned roughly over one quadrant of the subject's head. It is to be appreciated that other configurations are possible, with any other number of coils incorporated into a particular interface, as aspects of the invention are not limited in this respect. It is also to be appreciated that other configurations of coils may also be employed by embodiments of TMS devices, as aspects of the invention are not limited to the use of figure-eight coils.

Different electromagnetic coils of a single interface may be energized and fired in different manners. According to some approaches, each the plurality of electromagnetic coils are fired in unison. Alternately, the various coils may be fired at different times than one another, yet still according to a systematic pattern. In other embodiments, the coils may be fired randomly with respect to one another, as aspects of the invention are not limited in this respect.

Components of the TMS device may be packaged to promote rapid deployment and ease of use. FIG. 2B shows one embodiment of a TMS device that has a control box to incorporate all of the components of the device, except the interface and a connection therebetween. This configuration may provide a reduced number of components for a respondent to handle when operating the TMS device. In an emergent situation, the respondent may place the interface about the subject's head, and then attend to the controls on the control box. In this respect, operation may be simplified by reducing the number of steps to ready the TMS device for use on a seizing subject. Other configurations are also possible for promoting rapid deployment and ease of use, such as the configuration of embodiment of FIG. 2A, where the control box is attached directly to the interface.

Controls of the TMS device may be configured for simplified operation, such that respondents may be qualified to operate the TMS device with minimal prior training, or no prior training at all. The illustrative embodiment of FIG. 2A includes only an activation control (i.e., a button in the illustrated embodiment) and a power indicator light. Once properly positioned about a subject's head, a respondent depresses the activation button to begin operation of the TMS device. Other control and indicator configurations are possible, as aspects of the invention are not limited to those that are illustrated. Moreover, as discussed herein, some embodiments of TMS devices may be configured for different types of applications, where additional controls and the ability to actively program a device may be desirable.

Once the activation control has been depressed, the controller of the TMS device may cause the electromagnetic coil(s) to be energized by current from the power source, such that a fluctuating magnetic field is emitted to induce electric current in a subject's brain or portions thereof. According to one operating protocol, after emitting a first fluctuating magnetic field or series of fields, the TMS device may turn off until the activation control is again actuated by the respondent. In such embodiments, the controller may limit the number of times that the fluctuating magnetic field may be emitted, or may require a predetermined length of time to pass, such as 0.1 seconds or more, 1 second or more, 5 seconds or more, 10 seconds or more, or 15 seconds or more before activating the control a subsequent time will produce a subsequent fluctuating magnetic field.

Once activated, the controller may then run the TMS device without further intervention by the respondent, according to some embodiments. Single pulses or pulse trains of magnetic stimulation may be emitted according to a predetermined sequence, such as every 0.01 second or more, every 0.1 seconds or more, every second or more, every 2 seconds or more, or every 5 seconds or more or according to any other timing scheme. Pulse trains may also include individual pulses that are fired irregularly, according to a predetermined pattern, or even stochastically, as aspects of the invention are not limited to any one configuration of pulse or pulse train. Once the respondent identifies termination of the seizure, the operating protocol may also be stopped by activating an appropriate control on the TMS device, or simply by removing the interface from the subject.

The treatment of ongoing seizures may include directing an initial magnetic field to the brain of a seizing subject as either a single pulse of magnetic energy or a series of pulses of fluctuating magnetic energy that fluctuate at a particular frequency or that fluctuate irregularly (i.e., a "pulse train"). If the seizure does not stop, subsequent fluctuating magnetic stimulation having greater intensity, duration and/or frequency may be applied to the subject's brain. In this manner, the extent of the subject's exposure to the fluctuating magnetic field may be minimized to the intensity, duration and/or frequency necessary to end the seizure.

As used herein, the term "duration", when used with reference to the stimulation (i.e., fluctuating magnetic field) that is applied to a subject's brain, refers to the amount of time that elapses during the period of stimulation. Duration may be a short as 50 microseconds or shorter, such as for stimulation that comprises a single pulse of stimulation, or as long as several minutes, such as for long pulse trains of stimulation.

As used herein, the term "frequency" refers the rate at which individual pulses are emitted during a given duration of stimulation. Typically, low frequency pulse trains have frequencies that lie between 0.33 Hz and 1.0 Hz, although lower frequencies are also possible. Intermediate frequencies may range between 1 Hz and 20 Hz, and high frequency pulse trains often have frequencies between 20 Hz and 200 Hz, although greater frequencies are also possible. Additionally, it is to be appreciated that individual pulses emitted during a given duration may vary according to an irregular pattern, or even stochastically, as aspects of the invention are not limited in this respect. Frequency, as associated with such embodiments, may describe the average frequency at which pulses are fired, and should not be considered to be limited to rhythmic patterns of stimulation. Purposefully arrhythmic, asynchronous patterns of stimulation are also encompassed.

According to some embodiments, the magnetic field may increase in intensity, duration and/or frequency during a common operating protocol. For instance, an operation protocol may include emitting an initial magnetic field as a single, 200 microsecond pulse. Subsequent magnetic fields may comprise longer durations, such as 500 or more microseconds, 1000 or more microseconds, or even greater durations.

The intensity of the magnetic field (and induced intracranial electrical current) may be increased during the progression of an operating protocol. Typically, magnetic fields used during TMS range from 0.5 Tesla to 3.0 Tesla and the intensity required to stop an ongoing seizure may lie anywhere within this range for a given subject. As another technique to minimize the overall magnetic field exposure of a subject, embodiments of operating protocols comprise emitting magnetic fields of lower intensities during initial portions of the protocol, such as 0.5 Tesla or 1.0 Tesla, and emitting subsequent magnetic fields of greater intensities, as may be required if a subject's seizure persists.

The frequency of magnetic fields emitted during pulse trains may be altered during the progression of an operating protocol to help end a seizure. According to some embodiments, magnetic fields may comprise pulse trains of magnetic energy emitted anywhere between 0.33 Hz or lower and 200 Hz or higher. Frequencies may be altered anywhere among this range during a given operating protocol. Additionally, the time that elapses between pulse trains that are emitted by the electromagnetic coil may also be altered during a common operating protocol. By way of example, anywhere between 0.01 seconds and 30 seconds may elapse between emitting the first magnetic field of an operating protocol, either as a single pulse or a pulse train, and the second magnetic field of the operating protocol. The time elapsed between emitting the second and third magnetic fields may be increased or decreased relative to the time that is elapsed between the first and second fluctuating magnetic fields. This trend may continue throughout an entire operating protocol, or for portions of an operating protocol.

Embodiments of the TMS device may include electrodes configured to receive electric signals indicative of a subject's brain activity, much like an electroencephalogram (EEG). As illustrated, the electrodes may be incorporated directly into the interface of a TMS device. This may facilitate the rapid placement of the probes by a respondent in an emergent setting. The electric signals may be used to identify the onset of a seizure or to optimize the timing of the magnetic field emissions to coincide with ongoing activity in the subject's brain. Various TMS techniques guided by such electric signals received from the brain are discussed in U.S. Pat. No. 6,571,123 ('123), entitled "Method and Apparatus for Recording an Electroencephalogram During Transcranial Magnetic Stimulation," and U.S. Pat. No. 6,266,556, which are each hereby incorporated by reference in their entirety.

As shown in FIG. 2B, electrodes may be incorporated directly into the interface of a TMS device. Fastening the interface in place may bring the electrodes into appropriate contact with the subject's head, such that measurement of electric signals being transmitted in the subject's head may be sensed without requiring any additional steps for a respondent or healthcare professional that is administering TMS therapy.

The output of an EEG, or equivalently, the electric signals measured by embodiments of the TMS device, can be used to detect the onset of a seizure before a subject presents visible symptoms of the seizure. One approach to identifying seizure onset is to monitor the root mean square (RMS) value of the electric signals received by the electrodes. A baseline RMS level may first be established during a period of normal brain activity. A threshold RMS value may then be set that, when reached by the subject, indicates the potential onset of a seizure. One threshold value includes the baseline RMS value of a subject plus two times the standard deviation of the baseline RMS value, although others are also possible. Other similar approaches may comprise applying a Fourier transform to the output of the electrodes, and identifying frequency domain characteristics that indicate the potential onset of a seizure.

Detecting subclinical seizures through electroencephalograph-like monitoring may prove particularly useful in acute healthcare settings. Subjects that have been known to experience seizures, or who have conditions that are expected to lead to seizures, may be monitored with embodiments of the TMS device, according to the present invention. The onset of a seizure may be detected early, via electroencephalogram-like monitoring, such that seizure may be stopped early, even before there is visible evidence of the seizure occurring.

A subject's brain activity may also by assessed by the controller to identify optimal timing for the emission of fluctuating magnetic fields. As is to be appreciated, brain activity is typically characterized by the transmission of electric impulses across a wide variety of frequencies and is sometimes described as comprising "spikes and waves". The controller may process the electric signals received from the brain to quantify the type and amount of brain activity that is occurring. For instance, a Fourier transform may be applied to the output of the electrodes to identify various spectral components of the brain activity. This information can then be used to identify when, in time, a fluctuating magnetic field should begin to be applied to the subject. In this sense, the "phasing" of the operating protocol may be based on feedback from the subject.

Readings of electric signals being transmitted in the subject's brain may also determine the frequency at which fluctuating magnetic fields are applied to the subject's brain. Frequencies may be identified for magnetic fields that are directed to the subject's brains, particularly when the Fourier transform of signals received from a subject indicates that a seizing subject's brain activity is centered about one or more discrete frequencies. Directing a magnetic field of alternate frequency may better alter the brain's activity, and in doing so, end an ongoing seizure. It is to be appreciated, however, that not all embodiments are configured to emit fluctuating magnetic fields at specific frequencies, and that some may emit fluctuating magnetic fields characterized by a broad spectrum of frequencies, or even a single impulse of a magnetic field, as aspects of the invention are not limited in this respect. Additionally, in some embodiments, fluctuating magnetic fields are emitted stochastically.

The brain activity of a subject may also be monitored by embodiments of the TMS device to identify the end of a seizure. In some embodiments, the operating protocol may be terminated to reduce the overall magnetic field exposure of the subject, once there is confidence that an ongoing seizure has ended. As discussed herein, a baseline RMS value of the brain activity may be established along with a threshold value to identify the onset of a seizure. The baseline value may also be used to identify the termination of seizures, according to some embodiments. In other embodiments, a Fourier transform may be used to identify whether the systematic transmission of electric signals about the brain at particular frequencies, as is often associated with a seizure, has been replaced with more chaotic transmissions of varying frequency.

Embodiments of the TMS device may be configured for use in a healthcare facility or home, in addition to highly trafficked public venues. Embodiments may be configured differently for use in such settings. According to one embodiment, the controller may be mounted on stand that may be wheeled to a subject's bed who is in need of TMS therapy. The stand may position the controller at an appropriate height for the healthcare professional and subject undergoing TMS treatment. According to other embodiments, the TMS device may be incorporated into a portable case to facilitate transportation between medical facilities, to a subject's home, or anywhere else where a subject may use the device.

As discussed herein, another aspect of the invention relates to methods of non-invasively assessing positions of a subject's brain for the placement of intracranial electrodes. Such intracranial electrodes may be placed for long-term treatment of various conditions exhibited by a subject, including but not limited to Parkinson's disease, dystonia, and epilepsy. The permanent electrodes may include electrodes that provide electric current, heat, and/or cold, and the like, as aspects of the present invention are not limited in this respect.

According to one illustrative embodiment, candidate positions for the invasive placement of intracranial electrodes about a subject's brain are first identified. The fluctuating magnetic field of a TMS device is then, in turn, focused toward each of the candidate positions. The subject is observed for the presentation of intended and any unintended effects, such as partial paralysis or loss of speech, that might be associated with applying a fluctuating magnetic field in each candidate position. This process is repeated for all candidate positions. Each of the candidate positions may then be compared based on the existence or extent of unintended effects so that preferential positions, that exhibit minimal or no unintended effects, maybe identified for the potential placement of intracranial electrodes.

The extent to which applying a fluctuating magnetic field to each of the preferential positions causes an intended effect, such as stopping an ongoing seizure, may then be assessed so that a position can be chosen for the placement of an intracranial electrode. According to some embodiments, fluctuating magnetic field(s) are applied to each of the preferential positions during an ongoing seizure, or other event of interest, and the ability of the magnetic field to terminate the seizure is gauged. This process may be repeated for each of the preferential positions until one or more preferential positions are identified as optimal candidates for intracranial electrode placement.

As discussed herein, some applications of TMS may benefit by targeting specific areas of the brain. Once the appropriate area has been identified, it may be important that the same brain area is targeted across multiple TMS stimulations or sessions. TMS may be delivered via a hand-held or an articulated arm set by a physician or a properly trained technician so that the stimulation coil targets the desired part of the subject's brain. The specific area of the brain to be targeted is often determined using either scalp measurements (which are notably imprecise and introduce substantial inter-individual variability), or an MRI of the subject's brain in combination with a frameless stereotactic device.

After the identification of the brain area to be targeted, it may be beneficial to ensure that the same brain region is targeted throughout the treatment (e.g., throughout successive sessions), or that an alternate brain region may be targeted for subsequent TMS treatment or evaluation for the potential placement of an intracranial electrode. This may be achieved via monitoring using frameless stereotaxy and/or repeated adjustments by the physician or technician. Applicant has appreciated that a headpiece or helmet fitted to the subject's own head shape and that incorporates TMS coils positioned so as to target the desired brain region in the subject, would both facilitate portability and improve the consistency of coil positioning both during a session and between multiple sessions.

In conventional TMS therapy, identification of the brain area to be targeted as a result of a particular coil placement is often based on a concentric sphere model of the field of distribution of the induced magnetic fields and resulting current fields. Applicant has recognized that such models may be inaccurate, and subsequently result in application of fluctuating magnetic fields that target (e.g., that are focused and/or stimulate) unintended areas of the brain. Applicant has identified that a more accurate determination of brain target location may be determined by considering tissue characteristics of the individual subject undergoing treatment, as discussed in greater detail in International Patent Application No. PCT/US2007/005893, filed on Mar. 7, 2007 and U.S. Provisional Application No. 60/779,847, filed Mar. 7, 2006, each of which are hereby incorporated by reference in their entirety. For example, brain lesions (e.g., strokes) may markedly disrupt induced fields within the brain. Moreover, anisotropy and/or inter-individual variability may cause changes in the induced fields that are not captured by conventional head-models. Such considerations may cause substantial inaccuracy in computing the target location, for example, reducing the spatial precision in determining focal areas, and/or reducing the efficacy of the treatment and potentially increasing risks and undesirable side-effects.

Applicant has developed methods for guiding the placement of coils by considering characteristics of the tissue within the brain. One embodiment includes determining, at least in part, the distribution of one or more dielectric properties (e.g., conductivity, permittivity, permeability, etc.) in a portion of the brain to facilitate accurate positioning of one or more TMS coils. For example, identified dielectric characteristics of the brain may be used to determine the current density distribution that would result from a particular coil placement. The procedure may be used to determine a coil placement that induces a desired current density to an intended portion of the brain.

In one embodiment according to the present invention, TMS coil placement guided by dielectric property determination may be incorporated into a generally portable TMS helmet, facilitating individualized treatment by, for example, correcting for distortions that brain lesions or other individual brain characteristics impose on the TMS induced currents. However, such coil placement methods may be used with any TMS device, as the aspect of the invention are not limited in this respect.

Even when precision in targeting a specific brain region is high, the locality of effects of TMS may remain suboptimal. However, diffusion spectrum imaging (DSI), can be used to reveal tissue characteristics in order to maximize the focal specificity of the effect of TMS on a given brain region. DSI-guided TMS may be integrated to provide an optimal system to allow increased precision with respect to stimulating the brain with TMS. These solutions may be incorporated into a portable helmet TMS device, or other TMS device, as the aspects of the invention are not limited in this respect.

One embodiment according to the present invention includes a TMS helmet that can be kept with the subject and used at any desired location (e.g., at home, at a workplace, etc.). FIGS. 3A-E illustrate a headpiece, in accordance with one embodiment of the present invention. The headpiece includes an outer shell (shown in FIG. 3A) that houses various components that together facilitate performing one or more TMS procedures on an individual. As discussed above, placement of TMS coils varies depending on the procedure and the individual. For example, different treatments target different portions of the brain. In addition, individual subjects have different sized heads, which may need to be considered in the construction of an individualized headpiece or helmet.

Figure 3A:
FIGS. 3A-3E illustrate various components of a portable TMS device, in accordance with some embodiments of the present invention.
Figure 3B:
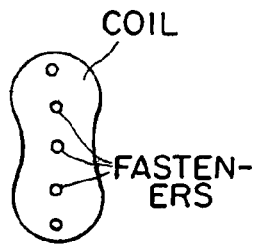

FIGS. 3B-3E illustrate one embodiment of a headpiece that can be individualized for a particular subject's treatment. FIG. 3B illustrates a TMS "figure-eight" coil similar to coils ubiquitously used in TMS procedures. However, the TMS coil includes a number of fasteners (e.g., snaps) that allow the coil to engage with an inner portion or skeleton of the headpiece that has been individualized for a particular subject's head. The fasteners may be of any number and of any type, as the aspects of the invention are not limited in this respect.

Figure 3C:
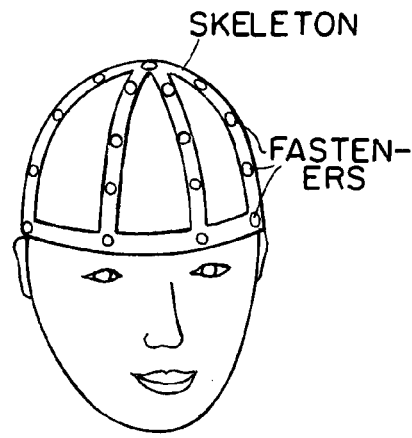

FIG. 3C illustrates an inner portion, referred to as a skeleton, according to one embodiment of the present invention. The skeleton may be made, for example, from a moldable plastic, or other material that can be shaped to an individual's head. Alternatively, the skeleton may simply come in a number of predetermined sizes that would allow the skeleton to fit a wide variety of head sizes. The skeleton may be formed from a number of strips, each strip including any number of fasteners adapted to engage with the fasteners on the TMS coil.

A physician or trained operator may determine the location on the head that the coil should be placed to carry out the intended treatment. The coil may then be fastened into place by engaging one or more (preferably two or more fasteners to prevent rotation) of the fasteners located on the coil and the fasteners located on the skeleton. It should be appreciated that any number of strips and any number of fasteners on the strips and/or coil may be used to ensure that the desired location has available fasteners to hold the coil at the desired. For example, any number cross strips may be added with fasteners to achieve a desired granularity with respect to the number of possible positions for the coil.

Figure 3D:
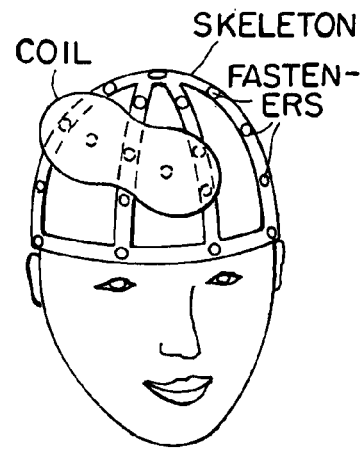
Figure 3E:
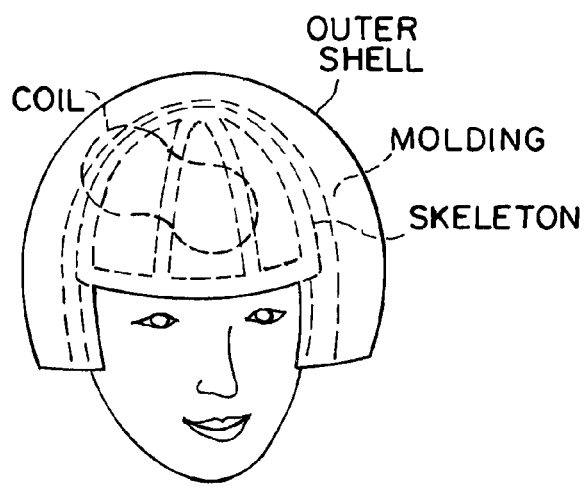

Alternatively, the location of the coil may be determined beforehand and the skeleton formed in accordance to make sure the precise intended location has available snaps for positioning the coil. For example, after the intended position of the coil has been determined, fasteners and/or strips may be positioned and arranged to form a skeleton that can engage the TMS coil at precisely the intended location. FIG. 3D illustrates the coil fastened to the skeleton at a position computed to carry out a particular treatment on an individual.

After the TMS coil has been fastened to the skeleton, the outer shell may be positioned over it to secure the coil and provide a protective barrier so that the subject cannot disturb the coil during and between treatments. In one embodiment, the outer shell contains a layer of moldable plastic, for example, material of the type used to make dental impressions or used in athletic mouthpieces. The outer shell may be heated so that the moldable plastic layer or molding becomes soft and pliant. The skeleton, with the attached coil may then be pressed into the molding. When the molding cools and hardens, the coil will be implanted in the molding and held firmly in place with the individualized and/or custom-fit skeleton. The hardened molding provides additional security against movement of the coil and provides an interface between the outer shell and the inner skeleton to form an integrated and personalized TMS headpiece.

Figure 4:
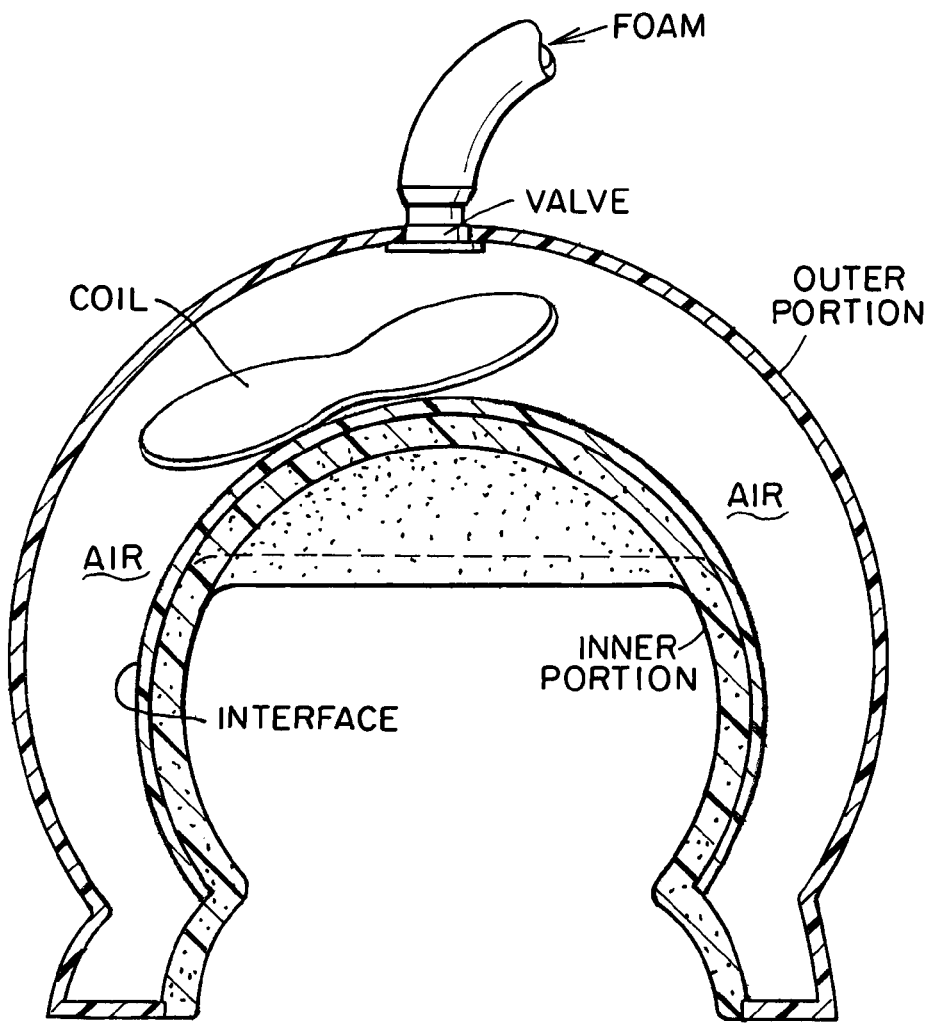
FIG. 4 illustrates a portable TMS device, in accordance with some embodiments of the present invention.

It may be advantageous to be able to reuse an outer portion of a headpiece (including the TMS coil) and have a disposable inner portion custom fit to a subject's head. FIG. 4 illustrates such a headpiece, in accordance with another embodiment of the present invention. The headpiece in FIG. 4 includes an inner portion that may be of any material that can be generally custom fit to an individual's head, such as foam rubber, moldable plastic, or any of the various padding materials used in athletic helmets such as football or motorcycle helmets. The headpiece also includes an outer portion formed from a generally rigid material having a hollow inner core. The inside of the outer portion and outside of the inner portion are designed to interface with one another, for example, as the padding in a football helmet interfaces with the hard outer shell.

Figure 5:
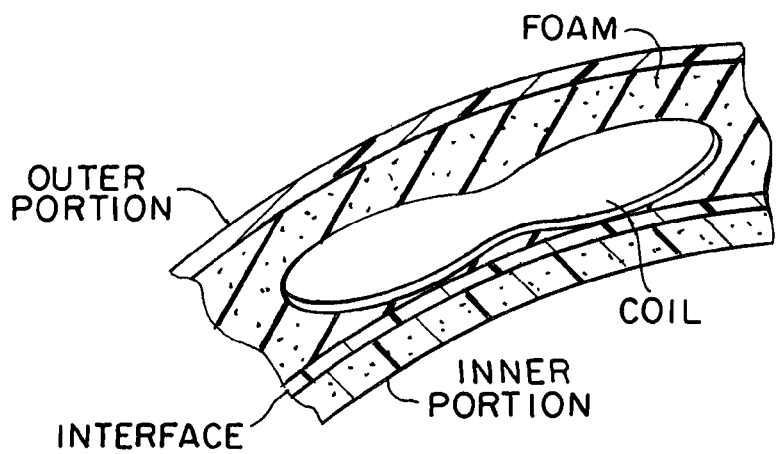
FIG. 5 illustrates a portion of a TMS device, in accordance with some embodiments of the present invention.

The headpiece also includes a valve adapted to connect to a hose or other foam applicator. Once the coil has been correctly positioned within the outer portion, foam may be applied through the valve to fill the open space in the hollow outer shell to hold the coil firmly in place. FIG. 5 illustrates a cross-section of the headpiece after the foam has been added. The foam may be a material that hardens to hold the coil in place, or may be any suitable material for securing the coil. In an alternative embodiment, the valve may be adapted to engage with a vacuum pump. After the coil has been positioned, the air may be pumped from the hollow shell to form a vacuum. The outer shell may be made from a material such as a plastic, that will collapse in a vacuum to firmly hold the coil in place (e.g., as in done in vacuum packing).

In another embodiment, the outer portion includes a number of moveable tracts to which the coil is attached. The tracts are arranged to give the coil a desired number of degrees of freedom and may be adapted to lock into place once the desired position has been reached. Any number of methods for positioning and securing one or more RF coils to a headpiece may be used, as the aspects of the invention are not limited in this respect.

As discussed above, there are treatments for a variety of different conditions and disorders. The treatments may vary in the duration of the stimulation, frequency of treatment, frequency and power level of the emitted fields, etc. In conventional TMS therapy, the variety of treatment types do not pose a difficulty because the subject must visit the hospital or doctor's office, where the appropriate procedure may be performed by the doctor or trained operator. However, various aspects of the invention are directed to portable headpieces that may be used by the subject at home.

Figure 6:
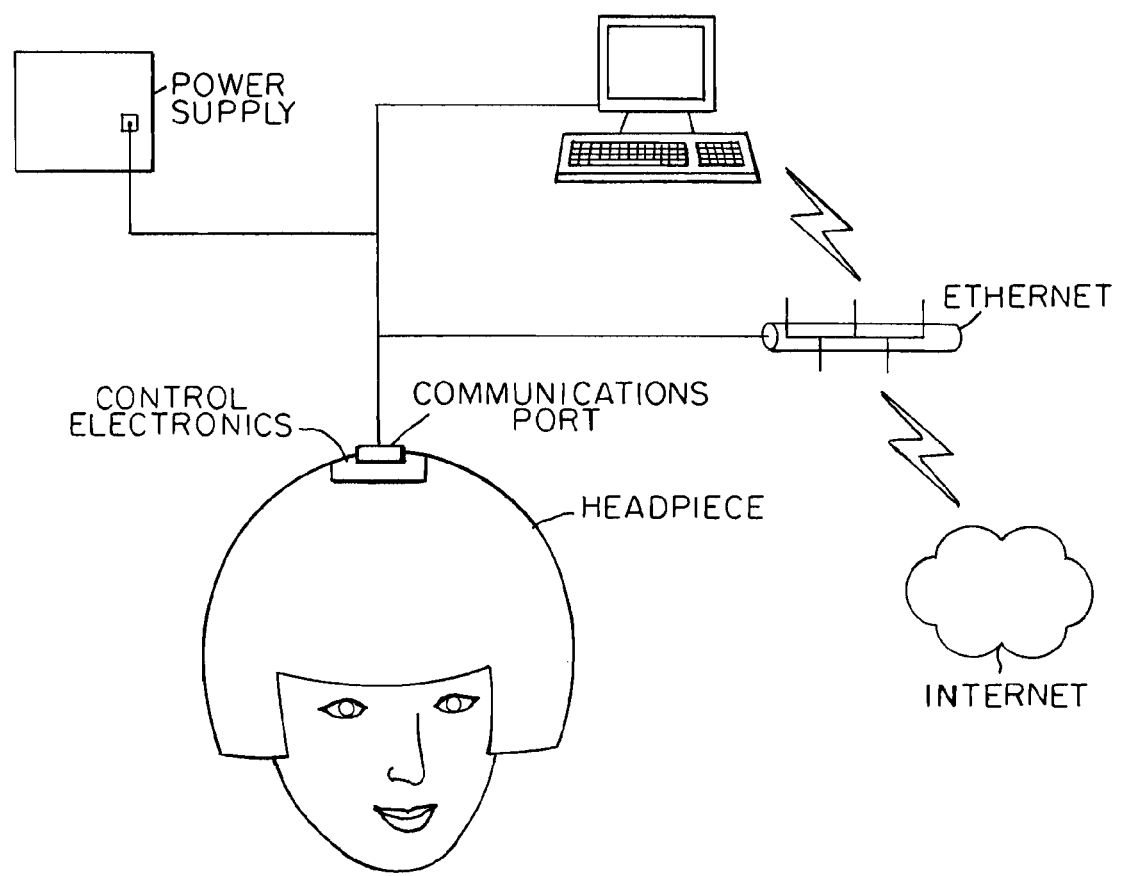
FIG. 6 illustrates a portable TMS device adapted to communicate over a network, in accordance with some embodiments of the present invention.

FIG. 6 illustrates a headpiece in accordance with one embodiment of the present invention. The headpiece illustrated in FIG. 6 includes a communications port having one or more electrical connections. For example, communications port may have a connection that allows the headpiece to connect to a local PC, to an Ethernet port and/or the Internet. In addition, the communications port may have a power connection that allows the headpiece to be connected to a power supply capable of generating power sufficient to drive the TMS coil to effect the desired TMS treatment. The headpiece may also include control electronics for controlling the application of power and the timing of the treatment. The control electronics may be hardware, firmware, software or a combination thereof, as the aspects of the invention are not limited in this respect.

Figure 7A:
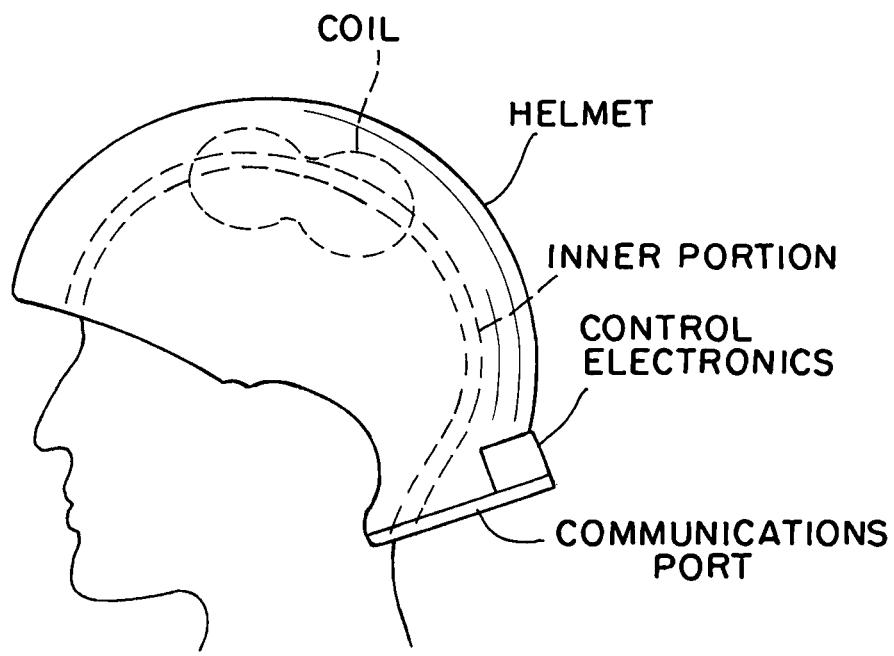
FIGS. 7A-7B illustrates a side-view and a bottom-view of a portable TMS device having a communications port, in accordance with some embodiments of the present invention.
Figure 7B:
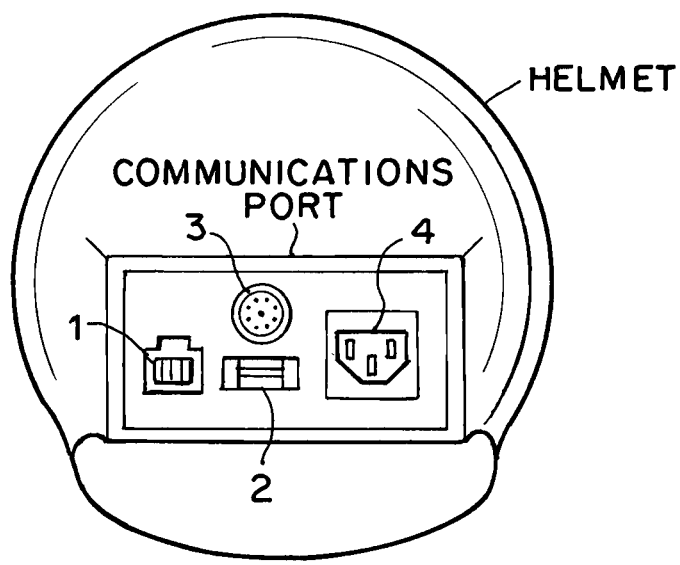

FIG. 7 illustrates a headpiece adapted for communications, in accordance with another embodiment of the present invention. The headpiece illustrated in FIG. 7 may include any of the components, positioning and/or securing mechanisms described above or any other positioning and securing means suitable for providing a headpiece that can be custom-fit for a particular subject's TMS treatment. FIG. 7A illustrates a side-view of the headpiece, including a communications port and control electronics integrated into the back portion of the headpiece. FIG. 7B shows the headpiece viewed from the bottom to better illustrate the communications port and control electronics.

The communications port includes a standard Ethernet connection 1 so that the headpiece may be connected to the Internet or to a local computer. The communications port also includes a Universal Serial Bus (USB) port 2 that can be used to connect the headpiece to standard personal computers or other peripheral devices, as discussed in further detail below. The communications port also includes a power connection 3 that can be used to connect to a power supply adapted for, or capable of, generating power sufficient to energize the coil at any of the standard TMS power levels used to provide stimulation. In addition, a standard power connection 4 may be used to connect to, for example, 60 Hz wall power to power, for example, any cooling mechanisms that the headpiece may require.

The Ethernet and/or USB port allows the headpiece to be connected to one or more programs configured to control the particular treatment of the subject in possession of the headpiece. For example, software installed on a local PC and programmed specifically for the subject's treatment may be provided to the control electronics to administer TMS sequences appropriate for the corresponding treatment. In addition, control electronics may also report back to the local PC about status or other information (such as verifying that the subject completed a session) that can be monitored remotely (e.g., via the internet) and adjusted if necessary by a physician without requiring the subject to make an office visit.

In one embodiment, a physician determines what should be the treatment for a particular subject and inputs that information to a program configured to administer treatments according to information provided by the physician, e.g., duration of each session, number of sessions per day/week/month, power level, pulse sequences, and/or subject information, diagnostic information etc. The customized program may be saved on a portable storage device such as a jump drive or flash drive, or other computer readable medium adapted to connect to, for example, the USB port of the headpiece. The control electronics may include one or more processors adapted to execute instructions saved on the portable storage medium. Accordingly, a physician can provide a customized treatment program that can be delivered via a portable storage device and connected to the headpiece to administered the saved treatment programs.

The headpiece may also be adapted to only operate via a control program (e.g., particular duration and session frequency, power levels, etc.). In this way, the subject cannot misuse the headpiece and administer TMS sessions that have not been approved and prescribed by the doctor. The headpiece may cease to operate after the treatment duration has expired, and may, for example, have an internal clock by which it will only operate according to the programmed treatment schedule. In addition, password information, fingerprint, voice and/or retinal analysis may be used so that only the targeted subject may use the device.

In addition, diagnostics can be obtained from the headpiece and transmitted to the physician to monitor the treatment. In one embodiment, EEG feedback is used to customize and/or optimize the treatment based on the electrical information of the subjects brain. For example, stimulation parameters may be set depending on the real-time physiologic parameters of the state of the subject's brain, thus guiding the subject's treatment according to the subject's recorded EEG, as discussed in further detail below. Other monitoring procedures can be done by the physician by real-time data obtained from the headpiece and transmitted over a network, e.g., the internet, via the communications port.

As discussed above, proper placement of a TMS coil may be an important factor in the effectiveness of TMS treatment. The identification of the brain area targeted by the placement of the TMS coil is conventionally performed using a concentric sphere model of the field distribution of the induced magnetic fields and resulting current fields. However, these models do not consider the tissue characteristics, anisotropy and inter-individual variation. Applicant has recognized that the dielectric properties (e.g., conductivity, permittivity, permeability, etc.) may disrupt the induced fields resulting from the TMS coil. As a result, the TMS coil may be positioned to stimulate the incorrect or unintended regions of the brain, limiting the efficacy of the treatment and increasing the risk of undesirable side-effects.

Applicant has appreciated that identification of the brain area targeted by a TMS coil that incorporates tissue characteristics, may improve the precision of TMS coil placement. In one embodiment of the present invention, tissue conductivity characteristics obtained from a subject's MRI are used to determine the placement of the TMS coil to stimulate a desired region of the brain. In another embodiment, one more dielectric properties of brain tissue are obtained from direct measurements of the subject's brain and used to determine the placement of the TMS coil to stimulate a desired region of the brain.

Figure 8:
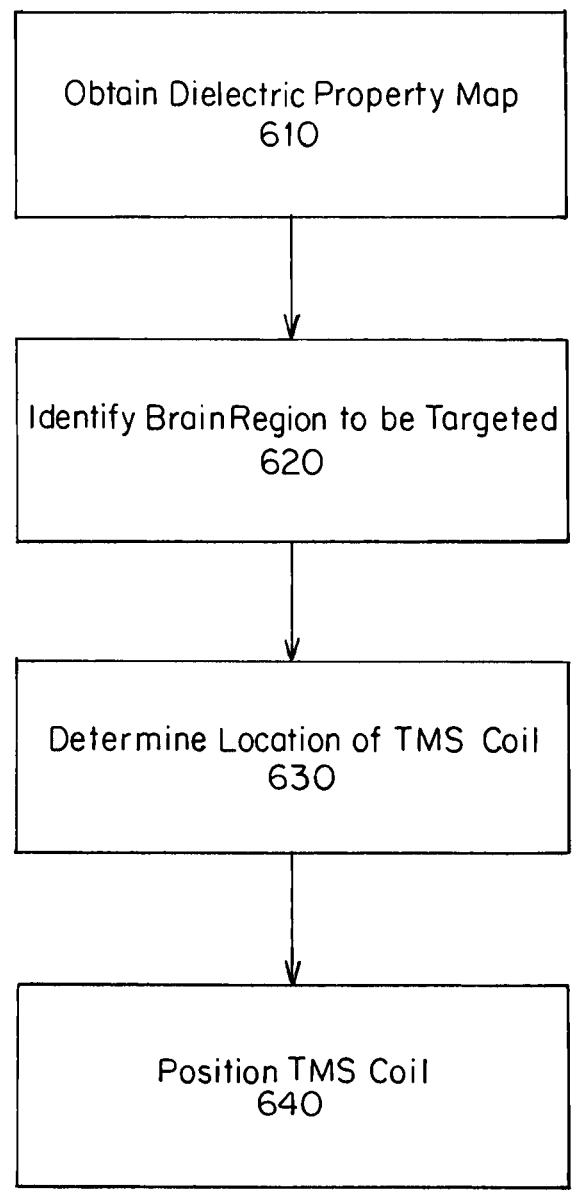
FIG. 8 illustrates a flow chart of a method for positioning a TMS coil, in accordance with some embodiments of the present invention.

FIG. 8 illustrates a method of positioning a TMS coil, in accordance with one embodiment of the present invention. In step 610, a dielectric property map of a subject's brain, or portion of the subject's brain is obtained. The term map refers herein to any information that associates a location in space with a value of one or more properties. Accordingly, a dielectric property map may be information that associates brain locations with one or more values of dielectric properties at the corresponding location. Various methods are known to obtain dielectric properties, such as from existing tissue property tables obtained from direct measurement, from MRI measurements of the subject's brain, various impedance mapping techniques, etc. Any one or combination of methods may be used to obtain a dielectric property map of the subject's brain or portion of the brain.

In step 620, the region of the brain to be targeted is determined. As discussed above, the region of the brain to be targeted typically depends on the type of treatment the subject is undergoing. In particular, the region of the brain to be targeted will depend largely on the condition that is being treated. Many types of conditions have been identified that may be treated by TMS, and the brain region to be targeted depends, at least in part, on the portion of brain responsible or associated with the condition being treated.

In step 630, the placement of the TMS coil is determined based on the region of the brain to be targeted and the dielectric property map. As discussed above, Applicant has identified that the dielectric properties of brain tissue affect the magnetic field distribution. As a result, to determine the precise placement of the TMS coil 640, changes in the magnetic fields due to the dielectric properties of the brain may need to be considered.

Applicant has developed methods of using the dielectric property map to compute the location of TMS coil placement to stimulate the intended region of the brain. Various methods of determining TMS coil placement based, at least in part, on one or more dielectric properties of brain tissue are described in detail in the Appendix. In particular, a model of the magnetic field distribution in the dielectric environment of the subject's brain may be used to compute the correct location of the TMS coil to stimulate the intended targeted area of the subjects brain. The methods provided in the Appendix are merely exemplary, and any method of computing TMS coil placement based, at least in part, on one or more dielectric properties may be used, as the aspects of the invention are not limited in this respect.

Applicant has appreciated that direction dependent changes in conductivity (i.e., conductivity anisotropy) have an impact on the predicted site and magnitude of the maximum cortical current density. In the presence of anisotropies, as seen in both healthy and pathologic brain tissue, relatively large conductivity dependent changes occur in the vector components of the induced current densities throughout the brain tissue, most prominently at the gray matter-white matter interface. Applicant has recognized that such direction dependent changes in conductivity can be discriminated via DSI imaging. DSI additionally provides a method to map principal white matter tracts in the brain and to resolve cyto- and myelo-architectonics of the cortex. This provides a method to investigate the orientation specificity of TMS, and allows comparison of TMS with electromagnetic models of the brain that include interactions with neuronal sub-populations in gray matter and subcortical white matter resolved with DSI.

Accordingly, Applicant has developed methods of improving guidance of TMS coil placement by including information about the direction dependent changes in conductivity, for example, derived from DSI measurements. Accordingly, field models used to determine coil placement from one or more dielectric properties of a portion of the brain may be extended to incorporate conductivity anisotropy and fiber tract information to improve the TMS coil placement algorithms.

Figure 9:
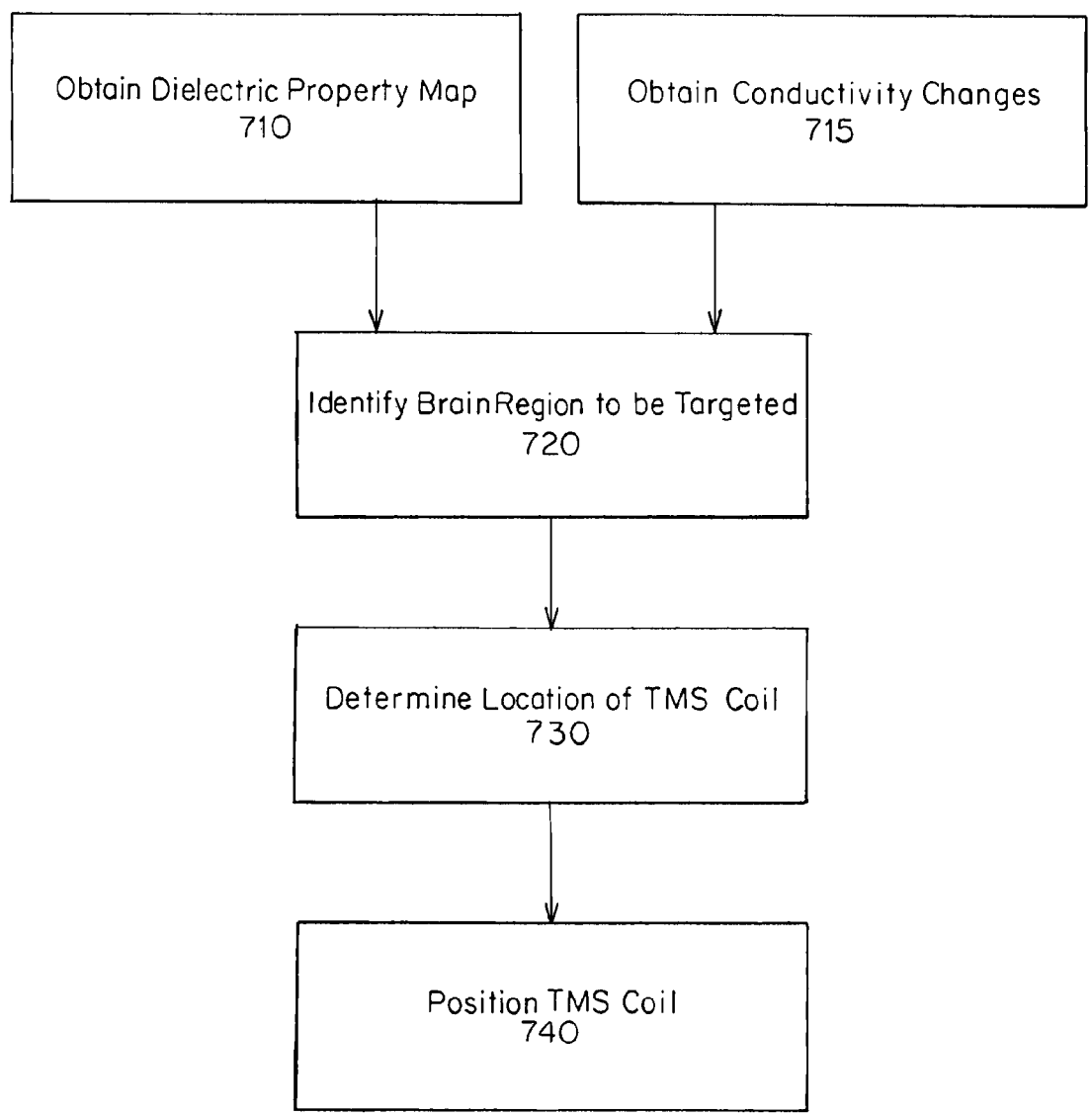
FIG. 9 illustrates a flow chart of another method for positioning a TMS coil, in accordance with some embodiments of the present invention.

FIG. 9 illustrates a method of positioning a TMS coil, in accordance with another embodiment of the present invention. The method illustrated in FIG. 9 may be similar to the method illustrated in FIG. 8. However, in step 715, conductivity anisotropy measurements and/or fiber tract information is obtained from one or more DSI images. Accordingly, in step 730, both the dielectric property information and the conductivity anisotropy measurements and/or fiber tract information are used to determine the appropriate location of the TMS coil. Various methods of using conductivity anisotropy and/or fiber tract information, for example, obtained from DSI images is discussed in further detail in the Appendix.

Figure 10:
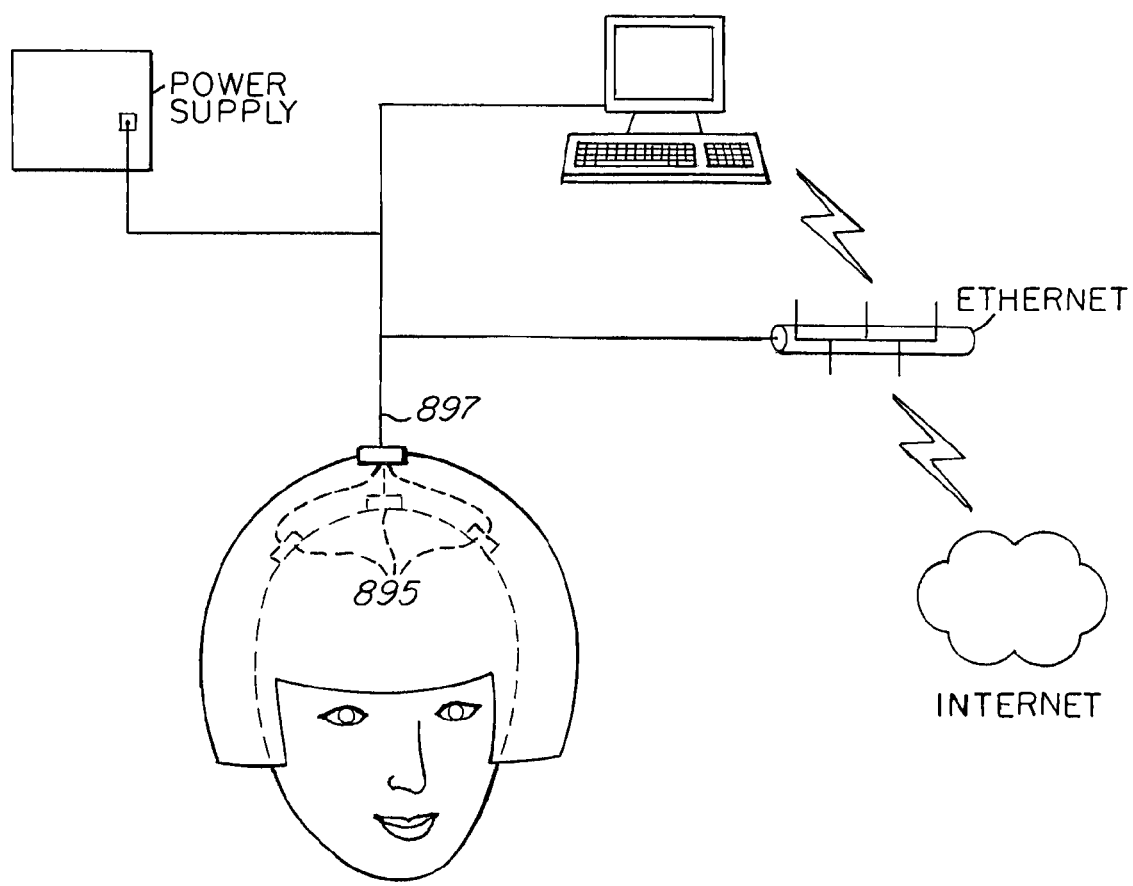
FIG. 10 illustrates a portable TMS device having EEG feedback, in accordance with some embodiments of the present invention.
Figure 11A:
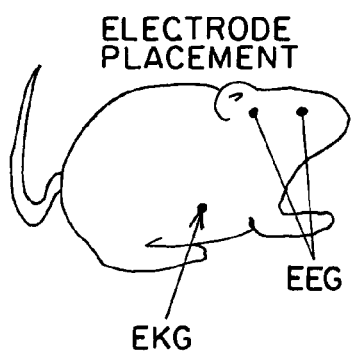
FIGS. 11A-11E illustrate one example of application of TMS methods to seizing rats.
Figure 11B:
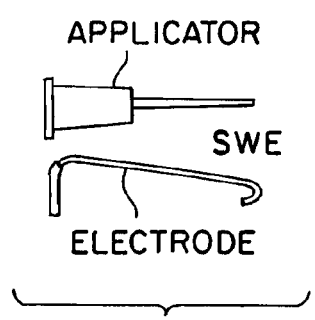
Figure 11C:
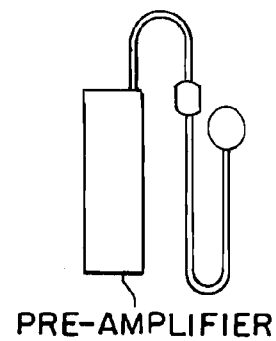
Figure 11D:
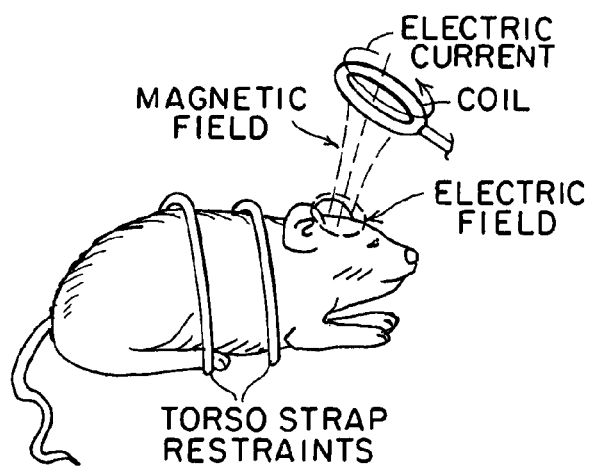
Figure 11E:
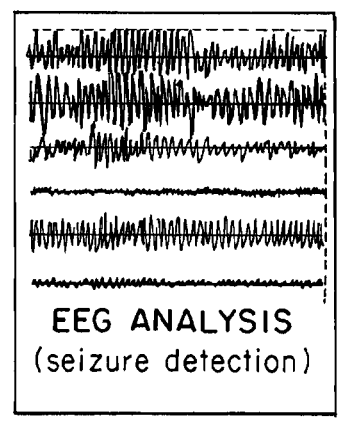

FIG. 10 illustrates a portable helmet having EEG electrodes incorporated into the helmet, in accordance with another embodiment of the present invention. In particular, electrodes 895 are positioned within the helmet to contact the subject's head. EEG signals are transmitted over communications means to control electronics and/or over the network to a remote location. The EEG signals may be automatically processed to adjust the TMS protocol based on the current state of the subject's brain, or the EEG signals may be analyzed remotely by a clinician who may provide control signals back to the helmet to optimally control the TMS protocol.

As discussed in incorporated U.S. Pat. No. 6,571,123, combined EEG and TMS may be used to maximize the efficacy of TMS treatments. Applicant has appreciated that the temporary state of activation of the subject's brain may impact both local and distant effects of TMS stimulation. Accordingly, by monitoring brain activity via EEG, the TMS protocol may be optimized real-time based on the subject's current brain state. The effects of TMS depend on the parameters of stimulation and on the specific brain region targeted. Applicant has appreciated that the impact of TMS spreads, from the directly targeted brain region along cortico-cortical and cortico-subcortical connections to influence a distributed cortico-subcortical, bi-hemispheric neural network.

Applicant has appreciated that the efficacy of TMS treatment may be improved by tailoring the TMS protocol (e.g., the stimulation parameters) based on EEG-like information. In particular, one or any combination of the level (strength) of the magnetic field, the duration of the stimulation, the polarity of the pulse, and the frequency of the stimulation may be adjusted based on the current state of the subject's brain as indicated by the EEG signal 897 provided by electrodes 895 incorporated into the portable helmet illustrated in FIG. 10.

It should be appreciated from the foregoing, there are numerous aspects of the present invention described herein that can be used independently of one another or in any combination. In particular, any of the above described operations or components may be employed in any of numerous combinations and procedures. For example, according to one embodiment, a portable headpiece or helmet unit, customized for an individual, is adapted for self-delivery of TMS treatment by the subject. The helmet is custom fit to the subject's head and encapsulates a TMS coil positioned to target a desired brain region with precision and consistency. The inner portion of the helmet may be tailored to an individual's anatomy without having to adjust an outer portion of the helmet (which may be reused). The helmet includes communications means to facilitate remote interactivity and control.

The TMS coil is positioned using an electromagnetic field model that incorporates dielectric properties of the subject's brain and/or conductivity anisotropy to facilitate positioning the TMS coil to stimulate the desired portion of the brain. The helmet also includes built-in electrodes for obtaining EEG measurements that allow a clinician to monitor the EEG and control the stimulation process based on the EEG, and remotely adjust the protocol based on subject response. However, it should be appreciated that other embodiments may not include one or more of the above components, or utilize one or more of the above operations. A headpiece may include any one or combination of the above features, as the aspects of the invention are not limited in this respect. It should also be appreciated that in some embodiments, all of the above-described components, features and operations can be used together in any sequence, or any combination or subset of the components, features and operations described above can be employed together in a particular implementation, as the aspects of the present invention are not limited in this respect.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

It should be appreciated that the various methods outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code. In this respect, it should be appreciated that one embodiment of the invention is directed to a computer-readable medium or multiple computer-readable media (e.g., a computer memory, one or more floppy disks, compact disks, optical disks, magnetic tapes, etc.) encoded with one or more programs that, when executed, on one or more computers or other processors, perform methods that implement the various embodiments of the invention discussed above. The computer-readable medium or media can be transportable, such that the program or programs stored thereon can be loaded onto one or more different computers or other processors to implement various aspects of the present invention as discussed above.

It should be understood that the term "program" is used herein in a generic sense to refer to any type of computer code or set of instructions that can be employed to program a computer or other processor to implement various aspects of the present invention as discussed above. Additionally, it should be appreciated that according to one aspect of this embodiment, one or more computer programs that, when executed, perform methods of the present invention need not reside on a single computer or processor, but may be distributed in a modular fashion amongst a number of different computers or processors to implement various aspects of the present invention.

Various aspects of the present invention may be used alone, in combination, or in a variety of arrangements not specifically discussed in the embodiments described in the foregoing, and the aspects of the present invention described herein are not limited in their application to the details and arrangements of components set forth in the foregoing description or illustrated in the drawings. The aspects of the invention are capable of other embodiments and of being practiced or of being carried out in various ways.

EXAMPLES

Example I

Anti-seizure effect of daily 1 Hz repetitive transcranial magnetic stimulation (rTMS) in a case of pediatric Rasmussen's encephalitis.

1 Hz rTMS was applied in daily sessions over the affected hemisphere to ameliorate intractable nearly-continuous right anterior focal seizures in a 14-year-old boy with progressive focal epilepsy, left hemiparesis and right hemisphere atrophy.

As explained above, rTMS is a method for noninvasive focal cortical stimulation that is based on the principles of electromagnetic induction. During rTMS small intracranial electrical currents are generated by a powerful fluctuating extracranial magnetic field. Low frequency (1 Hz) rTMS is emerging as a new therapeutic tool in epilepsy with a limited number of reports showing the capacity of rTMS to reduce seizure frequency and to interfere with ongoing seizures. We present a case of gradual seizure reduction with recurrent daily rTMS in a pediatric patient with Rasmussens encephalitis. The patient presented three months before treatment with frequent 2-3 minute seizures, generally separated by 0.5-1 minutes of interictal state.

1 Hz rTMS was applied with a figure-8 coil (1800 pulses per day at 100% motor threshold) in daily sessions over the right anterior seizure focus (F4-C4). Continuous EEG was recorded throughout the period. Mean seizure duration was calculated at baseline, during rTMS, and after rTMS on a daily basis.

During 1 Hz rTMS, average seizure duration was reliably decreased by 40% relative to baseline (n=68 seizures; p<0.01). In the first hour after treatment, seizure duration remained reduced by 30% (n=66 seizures; p<0.01). However, the anticonvulsive effect lasted less than 24 hours as baseline seizure duration was similar on each day.

1 Hz rTMS has a measurable anticonvulsive effect when delivered over continuously-seizing cortex, although the immediate effect may be short-lived. In such cases, repeated applications of rTMS, or replacement with durable neurostimulation, may be useful to maintain seizure suppression.

Example II

Figure 12A:
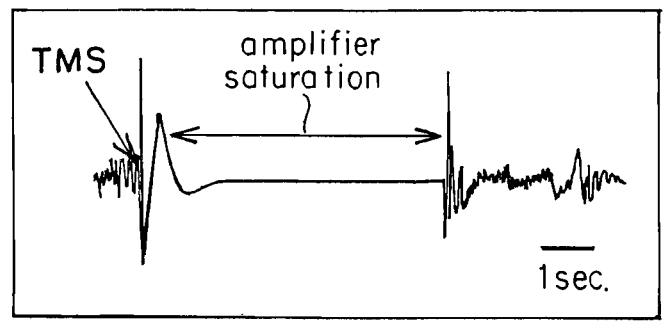
FIGS. 12A-12B illustrate reduced TMS artifacts with a slew-rate limited pre-amplifier.
Figure 12B:
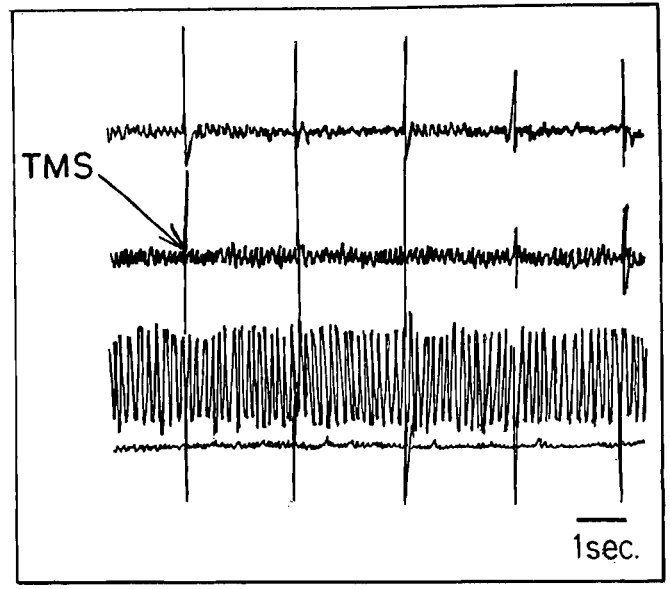

As shown in FIGS. 11A-11E, TMS methods were adapted for application to gently-restrained, seizing rats. EEG readings were recorded with three subdermal wire electrodes (SWEs). One SWE was placed on the torso to record EKG and two more wires were used as antennae to detect the TMS pulse and to identify timing of the pulse. Torso restraint permits clinical observation of seizures and full access of the head to the TMS coil. Slew-rate limited preamplifiers were included in series to the EEG acquisition system to minimize TMS-related amplifier saturation, as represented by FIGS. 12A and 12B, which show a reduced TMS artifact with slew-rate limited pre-amplifier.

Figure 14:
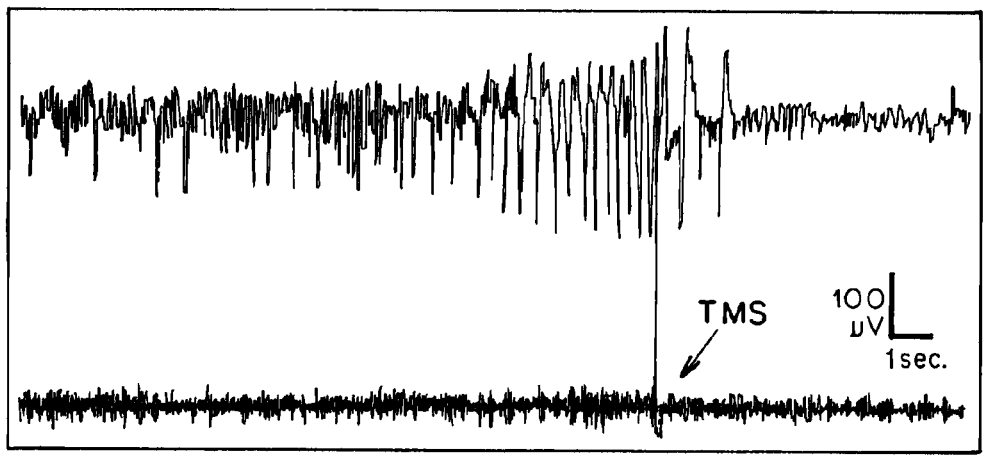
Figure 15A:
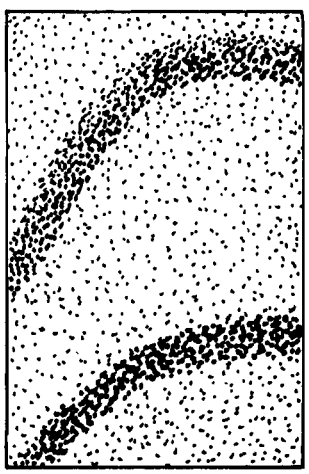
Figure 15B:
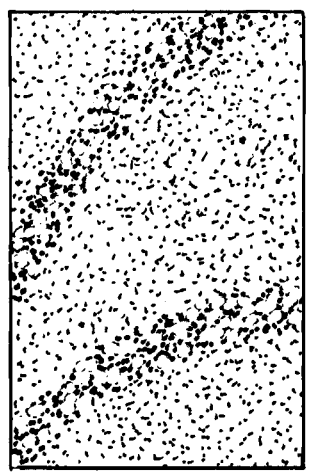
Figure 15C:
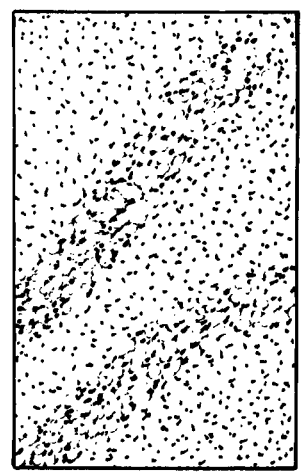

Seizures were induced with intraperitoneal kainate (KA) 11 mg/kg in young adult male Long-Evans rats. Real-time EEG was recorded and assessed for seizure discharges. A 0.5 H rTMS was applied during seizures with a figure-8 coil positioned overhead. A set of rats was sacrificed and perfused 2.5 hours after KA na KA+0.5 Hz rTMS for evaluation of c-Fos expression (a marker for seizure related excessive neuronal firing) in the hippocampus and dentate gyrus. Some results from the example are reflected in FIGS. 13-15.

Practical EEG-guided ictal TMS was found to be capable of being delivered with slew-rate limited preamplifiers. The SWE were also found to allow for quick, stable, TMS compatible EEG/EKG without surgery, mechanical or medical restraint. EEG-guided TMS was found to shorten seizure duration, as represented in Table 1 below. rTMS delivered during KA-induced status epilepticus was also found to inhibit seizure-related c-Fos expression in hippocampus and dentate gyrus.

TABLE 1

Summary of TMS effect on KA-induced seizure duration

| Deviation | N | Avg. Duration | Std. |
|---|---|---|---|
| Treated Seizures | 31 | 45.1 sec | ±23.2 sec |
| Untreated Seizures | 70 | 62.8 sec | ±43.3 sec | t-test: 2.75 (p = 0.007)

Example III

Figure 13:
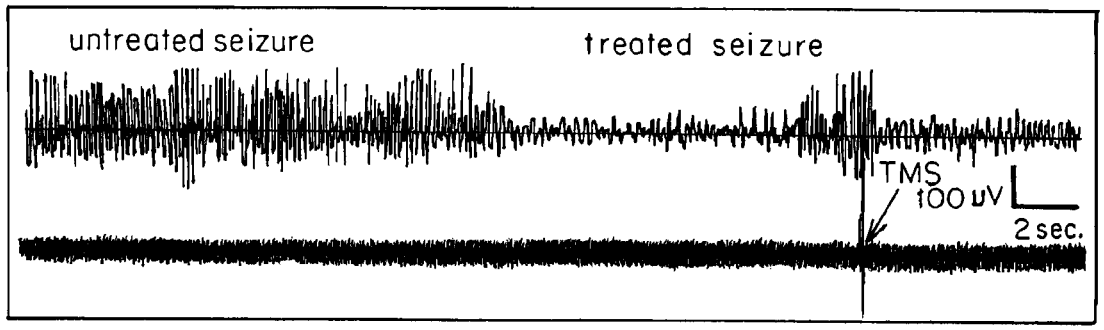
FIGS. 13-15 illustrate a spontaneous seizure in a rat being recognized and terminated with TMS.

EEG and TMS techniques were combined to enables a closed-loop system where seizures were recognized and treated with an electrical current induced by a fluctuating extracranial magnetic field. As shown in FIG. 13, a spontaneous seizure in a rat was recognized and terminated with TMS.

Example IV

Figure 16:
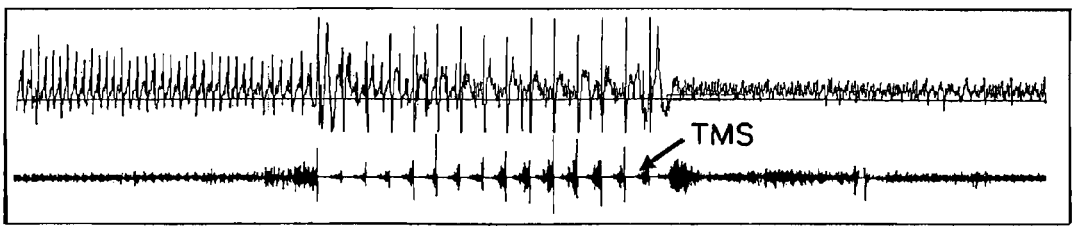
FIG. 16 illustrates EEG-guided TMS to enable when a seizure was stopped and when no further stimulation was required.

EEG-guided TMS enabled an operator and/or software to identify when a seizure was stopped and when no further stimulation was required, as demonstrated in FIG. 16 where a kainate-triggered seizure in a rat terminates after 15 consecutive stimuli delivered at 0.75 Hz.

Example V

Figure 17:
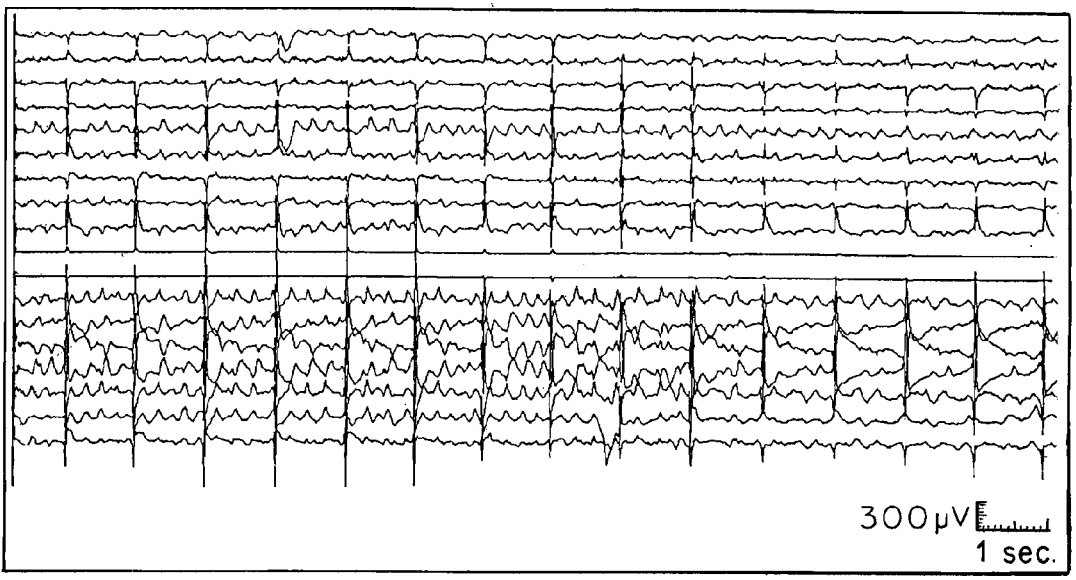
FIG. 17 shows the combination of TMS with EEG methods.

Ongoing EEG was combined with TMS in human subjects to enable real-time assessment of anticonvulsive effect by software or human operator. FIG. 17 shows the combination of TMS with EEG methods.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. As one example, it is to be appreciated that different types of electromagnetic waves, other than fluctuating magnetic fields, maybe used to induce intracranial electric currents with in a subject's brain, and in this sense, it is to be appreciated that the concepts herein are not limited to be accomplished through the use of TMS. Accordingly, the foregoing description and drawings are by way of example only.

The phraseology and terminology used herein is for the purpose of description and should not be regarded as limiting. The use of "including," "comprising," or "having," "containing," "involving," and variations thereof herein, is meant to encompass the items listed thereafter and equivalent thereof as well as additional items.

What is claimed is:

1. A device for treating a seizure, the device comprising:
  a plurality of electromagnetic coils that receive power from a power source to produce a magnetic field;
  a controller that controls operation of the plurality of electromagnetic coils according to an operating protocol, wherein the operating protocol includes delivering an initial magnetic field having an intensity and a duration and delivering a plurality of subsequent magnetic fields, each of the subsequent magnetic fields having an intensity and a duration that is greater than the intensity and duration of previously delivered magnetic fields, respectively;
  a plurality of electrodes configured to receive a signal indicative of brain activity in a subject and to provide an electrical signal to the controller, wherein the controller is configured to start the operating protocol at a time after an indication of onset of a seizure, wherein the time is determined by analyzing the electrical signal to identify when to deliver the initial magnetic field relative to the subject's brain activity, and wherein the controller is further configured to stop the operating protocol by identifying, from the electrical signal, an indication of termination of a seizure; and
  an interface that includes the plurality of electrodes and the plurality of electromagnetic coils, the interface configured to position the plurality of electrodes to receive the signal and to position the plurality of electromagnetic coils to deliver the magnetic field to a subject's brain to treat the seizure.

2. The device according to claim 1, wherein the controller is configured to control a number of subsequent magnetic fields and a time interval between subsequent magnetic fields.

3. The device according to claim 2, further comprising:
  a manual activation control that, when activated, causes the controller to initiate the operating protocol.

4. The device according to claim 3, wherein further manual activation of the manual activation control is required before subsequent magnetic fields of the operating protocol are delivered.

5. The device according to claim 1, wherein the controller is configured to perform analysis of the signal and to cause the electromagnetic coil to deliver a magnetic field that is phased to the brain activity.

6. The device according to claim 1, wherein the controller is configured to control a spatial distribution of each magnetic field, a number of magnetic fields, and a time interval between subsequent magnetic fields.

7. The device according to claim 1, wherein the controller is configured to detect onset of a seizure through analysis of the signal.

8. The device according to claim 7, wherein the controller is configured to compare the signal to a baseline indicative of normal brain activity to detect the onset of a seizure.

9. The device according to claim 7, wherein the controller is configured to monitor root mean squared values of the signal to detect the onset of a seizure.

10. The device according to claim 7, wherein the controller is configured to monitor frequency domain aspects of the signal to detect the onset of a seizure.

11. The device according to claim 1, wherein the operating protocol includes governing an activity of each one of the plurality of electromagnetic coils.

12. The device according to claim 1, wherein the operating protocol includes increasing the intensity and the duration of each subsequent magnetic field until the signal indicative of brain activity in the subject is a baseline value indicative of normal brain activity.

13. The device according to claim 1, wherein the operating protocol includes delivering a plurality of subsequent magnetic fields until a predetermined brain activity signal is detected.

14. The device according to claim 1, wherein the operating protocol includes delivering a plurality of subsequent magnetic fields until the controller is manually paused by an operator.

15. The device according to claim 1, wherein the controller is further configured to determine a frequency from spectral components of the subject's brain activity, and wherein the operating protocol includes delivering the initial magnetic field and at least a portion of the plurality of subsequent magnetic fields at the frequency.

16. A device for treating a seizure, the device comprising:
  a plurality of electromagnetic coils that receive power from a power source to produce a magnetic field;
  a controller configured to control operation of the plurality of electromagnetic coils according to an operating protocol and activate the operating protocol in response to detecting onset of a seizure, wherein the operating protocol includes delivering an initial magnetic field having an intensity and a duration and delivering a plurality of subsequent magnetic fields according to a predetermined sequence without manual operation until termination of the seizure is detected by the controller, each of the subsequent magnetic fields having an intensity and a duration that is greater than the intensity and duration of previously delivered magnetic fields, respectively;

a plurality of electrodes configured to receive a signal indicative of brain activity in a subject and to provide an electrical signal to the controller, wherein the controller is configured to determine a time after detecting onset of the seizure by analyzing the electrical signal to identify at least one feature of the subject's brain activity and determining when to deliver the initial magnetic field to the subject based on the at least one feature, and wherein the controller is further configured to activate the operating protocol at the determined time; and an interface that includes the plurality of electrodes and the plurality of electromagnetic coils, the interface configured to position the plurality of electrodes to receive the signal and to position the plurality of electromagnetic coils to deliver the magnetic field to a subject's brain to treat the seizure.

17. The device according to claim 16, wherein the controller is further configured to detect onset of a seizure through analysis of the signal.

18. The device according to claim 17, wherein the controller is further configured to compare the signal to a baseline indicative of normal brain activity to detect the onset of a seizure.

19. The device according to claim 17, wherein the controller is further configured to monitor root mean squared values of the signal to detect the onset of a seizure.

20. The device according to claim 17, wherein the controller is further configured to monitor frequency domain aspects of the signal to detect the onset of a seizure.

21. The device according to claim 16, wherein the controller is further configured to compare the signal to a baseline indicative of normal brain activity to detect termination of the seizure.

* * * * *